US009173692B1

(12) United States Patent
Kaloostian

(10) Patent No.: US 9,173,692 B1
(45) Date of Patent: Nov. 3, 2015

(54) COMPOSITE METAL AND BONE ORTHOPEDIC FIXATION DEVICES

(71) Applicant: STC.UNM, Albuquerque, NM (US)

(72) Inventor: Paul E. Kaloostian, Los Angeles, CA (US)

(73) Assignee: STC.UNM, Albuquerque, NM (US)

( * ) Notice: Subject to any disclaimer, the term of this patent is extended or adjusted under 35 U.S.C. 154(b) by 265 days.

(21) Appl. No.: 13/918,949

(22) Filed: Jun. 15, 2013

Related U.S. Application Data

(60) Provisional application No. 61/660,133, filed on Jun. 15, 2012, provisional application No. 61/660,107, filed on Jun. 15, 2012.

(51) Int. Cl.
*A61B 17/86* (2006.01)
*A61B 17/00* (2006.01)
*A61B 17/68* (2006.01)

(52) U.S. Cl.
CPC ............... *A61B 17/864* (2013.01); *A61B 17/68* (2013.01); *A61B 17/8605* (2013.01); *A61B 17/8625* (2013.01); *A61B 2017/00933* (2013.01); *A61B 2017/00964* (2013.01)

(58) Field of Classification Search
CPC ............. A61B 17/864; A61B 17/8605; A61B 2017/00964; A61B 2017/00933
See application file for complete search history.

(56) References Cited

U.S. PATENT DOCUMENTS

| | | | | |
|---|---|---|---|---|
| 5,019,079 A | * | 5/1991 | Ross | 606/312 |
| 5,098,435 A | * | 3/1992 | Stednitz et al. | 606/916 |
| 5,672,176 A | * | 9/1997 | Biedermann et al. | 606/271 |
| 6,045,554 A | * | 4/2000 | Grooms et al. | 606/304 |
| 6,162,225 A | * | 12/2000 | Gertzman et al. | 606/309 |
| 6,554,830 B1 | * | 4/2003 | Chappius | 606/246 |
| 6,953,463 B2 | * | 10/2005 | West, Jr. | 606/326 |
| 7,063,701 B2 | * | 6/2006 | Michelson | 606/307 |
| 8,323,543 B2 | * | 12/2012 | Michelson | 264/162 |
| 2001/0021852 A1 | * | 9/2001 | Chappius | 606/73 |
| 2002/0038123 A1 | * | 3/2002 | Visotsky et al. | 606/73 |
| 2003/0083662 A1 | * | 5/2003 | Middleton | 606/72 |
| 2003/0125744 A1 | * | 7/2003 | Contiliano et al. | 606/73 |
| 2003/0135214 A1 | * | 7/2003 | Fetto et al. | 606/72 |
| 2004/0225292 A1 | * | 11/2004 | Sasso et al. | 606/73 |
| 2005/0010226 A1 | * | 1/2005 | Grady et al. | 606/69 |
| 2006/0229622 A1 | * | 10/2006 | Huebner et al. | 606/73 |

(Continued)

*Primary Examiner* — Christian Sevilla
(74) *Attorney, Agent, or Firm* — Keith A. Vogt; Vogt IP

(57) ABSTRACT

Composite orthopedic devices that facilitate spine stabilization, such as: bone screws, rods, plates, interbodies, and corpectomy cages are disclosed. They are designed to provide both strength and load carrying capabilities, while increasing bio-integration of the devices with the surrounding bone tissue. They are constructed of composite layers of allograft and/or autograft bone and a structural material, such as titanium alloy or carbon/graphite fiber composite. Cannulations within the device are loaded with a mixture of stem cells, particles of allograft and/or autograft bone, and bone growth factors, such as BMP-2. The cannulations are connected to the surface of the device via multiple fenestrations that provide pathways to supply the bone/stem cell mixture to the surface, allowing living bone tissue to grow and insure bio-integration. The devices can also have radiofrequency (RF) stimulation implantation within the structure of the implanted device, capable of responding to external RF stimulation of enhanced bone growth.

11 Claims, 13 Drawing Sheets

(56) References Cited

U.S. PATENT DOCUMENTS

| | | | |
|---|---|---|---|
| 2009/0306725 A1* | 12/2009 | Hiromoto et al. | 606/298 |
| 2010/0042215 A1* | 2/2010 | Stalcup et al. | 623/16.11 |
| 2010/0160977 A1* | 6/2010 | Gephart et al. | 606/305 |
| 2012/0197311 A1* | 8/2012 | Kirschman | 606/304 |
| 2012/0323285 A1* | 12/2012 | Assell et al. | 606/305 |
| 2013/0110183 A1* | 5/2013 | Duggal et al. | 606/328 |

* cited by examiner

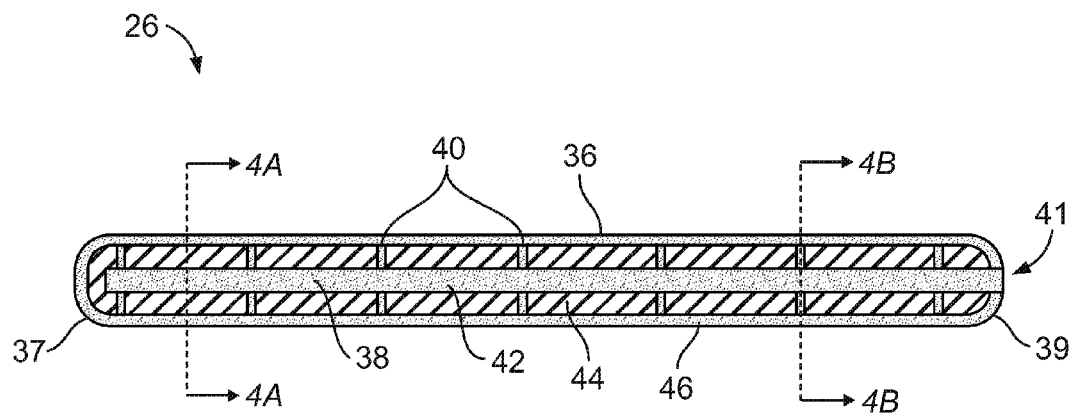
FIG. 4A
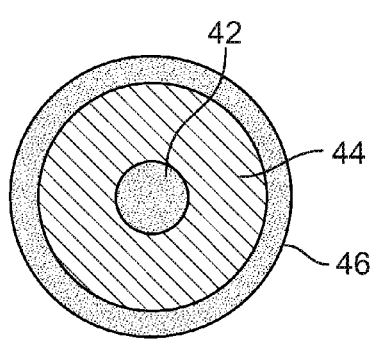 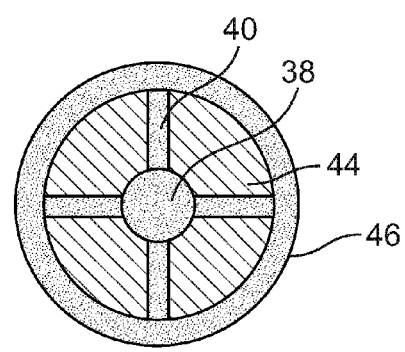
FIG. 4B  FIG. 4C

FIG. 8A  FIG. 8B

COMPOSITE METAL AND BONE ORTHOPEDIC FIXATION DEVICES

CROSS-REFERENCE TO RELATED APPLICATIONS

This application claims the benefit of U.S. Provisional Patent Application by Paul E. Kaloostian, Ser. No. 61/660,133, "Device for Guiding and/or Forming a Hole in Bone Tissue and Methods of Use", filed Jun. 15, 2012; and also U.S. Provisional Patent Application by Paul E. Kaloostian, Ser. No. 61/660,107, "Orthopedic Devices and Methods of Use", filed Jun. 15, 2012; both of which are incorporated herein by reference.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE INVENTION

1. Field of the Invention

The present invention relates generally to orthopedic fixation devices, fasteners, and implants that are used in orthopedic surgery, neurosurgery, plastic surgery, hand surgery, foot and ankle surgery, and Ear-Nose-Throat (ENT) surgery. These devices, such as: pedicle screws, rods, cross-links, plates, set capping screws, spinal fusion interbody spacers for lumbar/thoracic/cervical spine (both stand alone and with associated interbody and plate combination, and corpectomy cages (both stand alone devices and separate corpectomy and plate combinations), among others, are used, for example, to facilitate spine stabilization and healing after spinal fusion surgery; in addition to being used to stabilize other types of orthopedic bony fractures (such as long-bone or facial fractures) in trauma departments. Some of these devices may also be used in plastic surgery and oral/facial surgery, hand and foot surgery, and ear-nose-throat surgery for a variety of pathologies, including mandibular and facial fractures, extremity fractures, oncologic disease of the skeleton and skull, and traumatic disease of the skeleton and skull.

2. Description of Related Art

Millions of people suffer from a variety of musculoskeletal disorders or traumatic occurrences necessitating the use of methods and devices to provide reliable spinal stabilization and facilitate rapid healing. Stabilization may be accomplished with mechanical fasteners, implants, and fixation devices such as pedicle screws, rods, cross-links, plates, vertebra interbody spacers, and corpectomy cages.

Pedicle screw fixation has been shown to be superior to other methods of instrumentation of the lumbar and thoracic spine for spinal fusion and correction of deformity. However, there are many complications associated with placement of screws within the lumbar and thoracic spine, as well as the entire spinal axis. Pedicle perforation is noted to be as high as 40%, which increases likelihood of dural tears, nerve root injuries, paraplegia, and vascular injury.

Non union and pseudoarthrosis rates have been shown to be as high as 10% to 40%. Screw pullout rates are noted to be as high as 5-20%. Infection continues to be a devastating problem post-operatively in patients with spinal instrumentation and fusion.

Surgical techniques for the treatment of spinal injuries or deformities (e.g., scoliosis) are usually aimed at joining together two or more adjacent vertebrae of the spine, through a procedure that is called spinal fusion. A common approach to spinal fusion adopts a fixation system that is anchored to the spine by way of orthopedic screws implanted into the pedicles of two or more adjacent vertebrae. The single screws (i.e., pedicle screws) are connected together by means of rigid or semi-rigid rods, thereby forming a rigid cage that stabilizes and protects the spine. In previous versions, the connecting rod was housed within a transversal hole provided in the pedicle screw head itself. However, due to the irregularity of bone anatomy, it was unlikely that once the screws had been implanted into the spine pedicles that the transverse holes in their heads would be properly aligned for rod insertion. Hence, in order to facilitate the alignment and insertion of the rod, modern pedicle screws are provided with a rotatable, rod-receiving connecting member (connector) that freely rotates and swivels with respect to the screw's shaft.

Screws of this type, named polyaxial screws, comprise a threaded shaft with a hemi-spherical polyaxial. The polyaxial drive end is typically housed inside a mating, hemi-spherical recess (i.e., as a ball & socket joint) provided in the rod-receiving connecting member (rod-connector). A transversal hole, or U-shaped channel, in the rod-connector houses the connecting rod; and a set-screw or threaded-plug insert is provided above the rod, which clamps the rod into a rigid, locked position. In typical polyaxial pedicle screws, such as the example disclosed in U.S. Pat. No. 5,672,176, the locking action of the set-screw determines the locking of both the connecting rod and the bone screw's orientation, since pressure applied by the set-screw is transmitted to both the connecting rod and the screw's hemi-spherical drive head.

These implantable, orthopedic fixation devices are typically made of a rigid material, such as a titanium alloy or stainless steel. While the use of such rigid materials provides sufficient strength and load-carrying capabilities to avoid fractures or breakage, the interface between the metallic device and the surrounding bone is relatively non-flexible and unyielding.

Alternatively, these devices may be formed of semi-rigid materials, such as polymeric materials (e.g., PEEK). While the use of such semi-rigid materials provides a more flexible or yielding interface between the device and the surrounding bone, the strength and structural load carrying capabilities of polymeric bone anchor are generally less than metal alloys.

Bone autograft and allograft and/or autograft materials are a third alternative, and they are commonly used for vertebra interbody fusion spacers, in part, due to their capability for bio-integration at bone-to-bone interfaces. While bone is quite strong in compressive loading, it is relatively weak in tension and shear. For this reason, structural (load-bearing) orthopedic fixation devices and fasteners (e.g., pedicle screws) are not often made of allograft (cadaver bone) and/or autograft bone tissue.

Thus, there remains a need for improved materials for use in orthopedic fixation devices, implants, and fasteners, especially for spinal stabilization, which optimally combine the best properties of all three types of materials described above; and corresponding methods for implementing same.

BRIEF SUMMARY OF THE INVENTION

Accordingly, the inventor herein discloses innovative orthopedic fixation devices and methods, such as pedicle screws, rods, plates, set-screws, spinal interbody spacers, and cages, to facilitate healing of fractured bones and for spine stabilization. The innovative devices are made of composite materials comprising both bone and metal, in a variety of compositions and geometric configurations; that are designed to provide both the necessary strength and load-carrying capabilities, along with means and methods for enhanced bio-integration of the devices with the surrounding bone tissue.

Thus, in a typical embodiment, the present invention provides an orthopedic bone screw for use in a surgical procedure. The screw can comprises a polyaxial, hemi-spherically shaped drive head, and a body. The body comprises a distal tip; and a threaded shaft extending from the drive head to the distal tip, wherein the shaft comprises a cannulation extending from the drive head along at least a portion of the length of the shaft; wherein the cannulated portion of the shaft contains a least one radial fenestration connecting the cannulated portion to the outer surface of the screw; wherein the bone screw is constructed of a composite material comprising allograft and/or autograft bone and a metal or metal alloy.

In various embodiments, the bone screw may be constructed with a multi-layered composite structure comprising a core and two layers; wherein the core is made of allograft and/or autograft bone, the middle layer is a metal or metal alloy, and the outermost layer is allograft and/or autograft bone. In certain embodiments, the bone screw may be constructed of a material comprising about 50% allograft and/or autograft bone and about 50% metal or metal alloy. In some embodiments, each layer (core, middle, and outer) has approximately the same radial thickness (i.e., ⅓, ⅓, ⅓). In various embodiments, the metal or metal alloy may be a titanium alloy, cobalt-chromium alloy, niobium alloy, and tantalum alloy. In another embodiment, the titanium or metal parts are replaced with carbon or graphite fiber reinforced parts in similar ratios as described above with the titanium embodiment.

In another embodiment, the bone screw has a torque shear of at least 0.10-0.20 newton-meters. In another embodiment, the bone screw has a pullout force of 500-700 Newtons.

Still referring to the bone screw, the shaft may be threaded from the drive head to the tip. In another embodiment, the threaded shaft tapers outwardly adjacent to the drive head to form a tapered undercut for the drive head in such a way allowing the drive head to rotate close to 90 degrees in all directions, with 360 degrees rotational capacity of the drive head. In another embodiment, the cannulated portion of the shaft contains a plurality of fenestrations that connect to the center of the screw, and the fenestrations may be spaced so as to occur every two full rotations of the threaded shaft. In another embodiment, each fenestration may be square and 2 mm in width and height.

Still referring to the bone screw, the allograft and/or autograft bone may be cancellous or cortical bone, or a combination of both. In another embodiment, the bone screw is coated with an antibiotic solution. In another embodiment, the cannulated portion of the shaft is filled with stem cells. In various embodiments the cannulated portion of the shaft is filled with small particles of allograft and/or autograft bone.

In various embodiments, the present invention provides a rod for use in a surgical procedure comprising a shaft having a first end and a second end wherein the shaft defines a cannulation extending along at least a portion of the length of the shaft; wherein the cannulated portion of the shaft contains a least one fenestration connected to the center of the rod, wherein the rod may be constructed of a material comprising allograft and/or autograft bone and a metal or metal alloy.

In another embodiment, the rod may be constructed of a material comprising a core and two layers; wherein the core is allograft and/or autograft bone, the middle layer is a metal or metal alloy, and the outermost layer is allograft and/or autograft bone. In certain embodiments, the rod may be constructed of a material comprising about 50% allograft and/or autograft bone and about 50% metal or metal alloy. In various embodiments, the metal or metal alloy may be titanium, cobalt-chromium, niobium alloy, and tantalum alloy. In another embodiment, the titanium or metal parts are replaced with carbon or graphite fiber reinforced parts in similar ratios as described above with the titanium embodiment.

Still referring to the rod, the allograft and/or autograft bone may be cancellous or cortical bone. In another embodiment, the rod is coated with an antibiotic solution. In another embodiment, the cannulated portion of the shaft may be filled with stem cells. In various embodiments the cannulated portion of the shaft may be filled with allograft and/or autograft bone.

Other composite orthopedic devices, such as composite bars or composite strips, can be constructed in a manner and fashion similar to the composite rod described above.

In various embodiments, the present invention provides a plate for use in a surgical procedure comprising: a body defining a posterior side, an anterior side, a first end and a second end; a first bone screw bore at the first end and configured to cooperate with a first bone screw to retain the first bone screw at a first determinative position relative to the body; and a second bone screw bore at the second end and configured to cooperate with a second bone screw to retain the second bone screw at a second determinative position relative to the body, wherein the plate contains a least one fenestration connecting to the center of the plate from the posterior side to the anterior side; and wherein the plate is constructed of a material comprising allograft and/or autograft bone and a metal or metal alloy.

In another embodiment, the plate may be constructed of a material comprising a core and two layers; wherein the core is allograft and/or autograft bone, the middle layer is a metal or metal alloy, and the outermost layer is allograft and/or autograft bone. In certain embodiments, the plate may be constructed of a material comprising about 50% allograft and/or autograft bone and about 50% metal or metal alloy. In various embodiments, the metal or metal alloy may be titanium, cobalt-chromium, niobium alloy, and tantalum alloy. In another embodiment, the titanium or metal parts are replaced with carbon or graphite fiber reinforced parts in similar ratios as described above with the titanium embodiment.

Still referring to the plate, the allograft and/or autograft bone may be cancellous or cortical bone. In another embodiment, the plate is coated with an antibiotic solution. In another embodiment, the fenestration may be filled with stem cells. In various embodiments the fenestration may be filled with allograft and/or autograft bone.

In various embodiments, the present invention provides a spinal fusion interbody spacer comprising: a body having superior and inferior abutment surfaces sized and shaped to be adapted to abut against adjacent spaced vertebrae; and said body having concave lateral side surfaces, wherein the spacer contains a least one fenestration from the inferior surface to the superior surface; and wherein the spacer is constructed of a material comprising allograft and/or autograft bone and a metal or metal alloy.

In another embodiment, the interbody spacer may be constructed of a material comprising a core and two layers; wherein the core is allograft and/or autograft bone, the middle layer is a metal or metal alloy, and the outermost layer is allograft and/or autograft bone. In certain embodiments, the interbody spacer may be constructed of a material comprising about 50% allograft and/or autograft bone and about 50% metal or metal alloy. In various embodiments, the metal or metal alloy may be titanium, cobalt-chromium, niobium alloy, and tantalum alloy. In another embodiment, the titanium or metal parts are replaced with carbon or graphite fiber reinforced parts in similar ratios as described above with the titanium embodiment.

Still referring to the interbody spacer, the allograft and/or autograft bone may be cancellous or cortical bone. In another embodiment, the interbody spacer is coated with an antibiotic solution. In another embodiment, the fenestration may be filled with stem cells. In various embodiments the fenestration may be filled with allograft and/or autograft bone.

A set screw cap that is used to fasten the screw onto the rod, can be manufactured with all of the same concepts presented above. In another embodiment, the titanium or metal parts are replaced with carbon or graphite fiber reinforced parts in similar ratios as described above with the titanium embodiment.

A corpectomy cage, either stand alone with attached plate on superior and inferior ends on anterior aspect of cage, or in isolation without associated plate, can be manufactured with all of the same concepts presented above. The titanium or metal products in another embodiment may be replaced with carbon fiber product in exact ratio as described above with the titanium embodiment.

Each of the above constructs presented may also be implanted with a radiofrequency stimulation capability. This will enable placement of external source of stimulation to the implanted radiofrequency implant allowing for increased fusion to occur.

External radiofrequency stimulation can be used with placement of patch on side requiring increased fusion (i.e., fractured extremity and spine). The titanium or metal products in another embodiment may be replaced with carbon fiber product in exact ratio as described above with the titanium embodiment.

In various embodiments, the present invention provides a method of using a bone screw in a surgical procedure comprising; providing a bone screw as described above; and inserting said bone screw into a bone.

In various embodiments, the present invention provides a method of using a rod in a surgical procedure comprising; providing a rod as described above; and fastening the rod to a bone.

In various embodiments, the present invention provides a method of using a plate in a surgical procedure comprising; providing a plate as described above; and fastening the plate to a bone.

In various embodiments, the present invention provides a method of using a spinal fusion interbody spacer in a surgical procedure comprising; providing a spinal fusion interbody spacer as described above; and fastening the spinal fusion interbody spacer to a bone.

In various embodiments, the present invention provides various methods for growing a coating/layer of living bone tissue on the exterior surface of the orthopedic device, either before or after the device has been surgically implanted.

In one example, the method can comprise: (1) providing a central reservoir (e.g., a cannulated portion) comprising a supply of precursor bone material (i.e., a "bone cocktail") comprising a mixture of stem cells, small particles of allograft and/or autograft bone, and (optionally) bone growth factors, such as BMP-2; then (2) migrating said mixture through fenestrations that are fluidically-connected to the central reservoir at one end of the fenestration and to the outer surface of the device at the other end of the fenestration; (3) migrating/flowing said bone precursor mixture onto the exterior surface of the device; and, finally, (4) transforming, over time, the bone precursor mixture into a continuous, consolidated layer of solid, living bone tissue that has the capability to infiltrate and bond to a patient's pre-existing bone structure, thereby enhancing bio-integration of the orthopedic device or implant.

BRIEF DESCRIPTION OF THE SEVERAL VIEWS OF THE DRAWINGS

The details of the present invention, both as to its structure and operation, may be gleaned in part by study of the accompanying drawings, in which like reference numerals refer to like parts.

FIGS. 4A is a cross-section longitudinal view of an embodiment of a rod for use in a surgical procedure.

FIGS. 4B and 4C are cross-section end views of an embodiment of a rod for use in a surgical procedure.

FIG. 8A is a cross-section view of the embodiment shown in FIG. 6 along Section 8A-8A after being filed with a bone growth mixture.

FIG. 8B is a cross-section view of the embodiment shown in FIG. 6 along Section 8B-8B after being filed with a bone growth mixture.

DETAILED DESCRIPTION OF THE INVENTION

Abbreviations and Definitions

Figure 1:
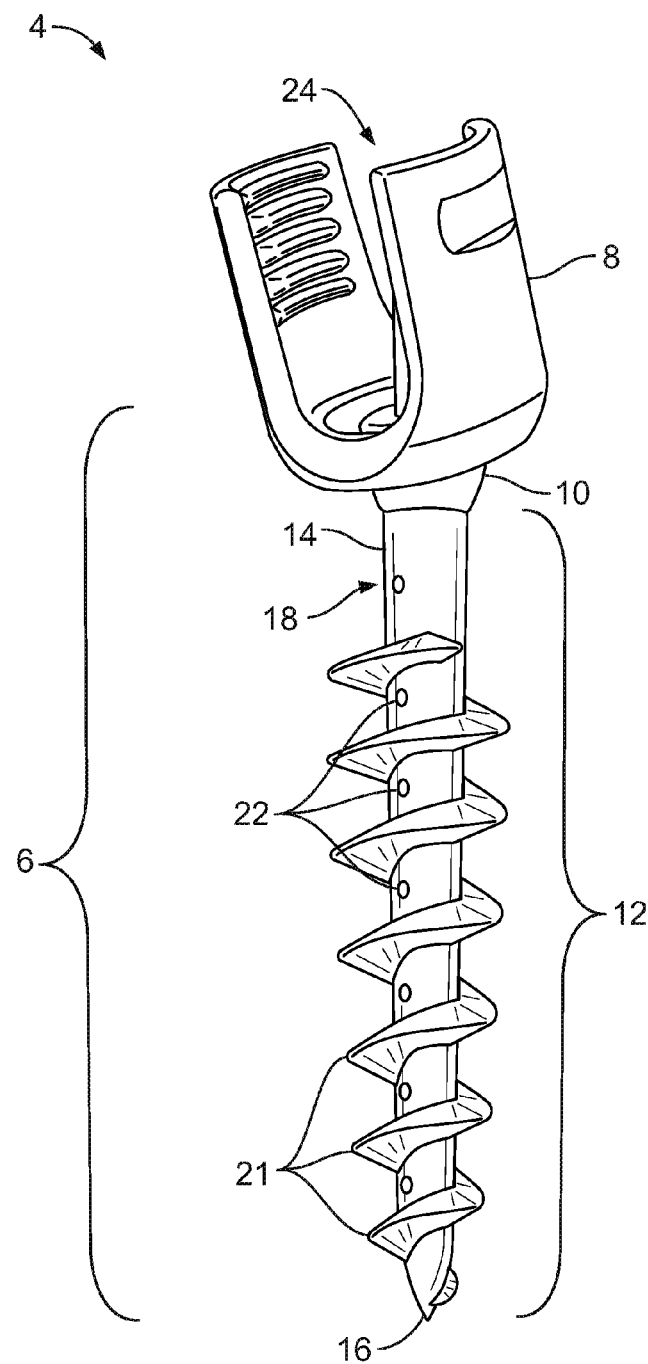
FIG. 1 is an isometric, side view of an example of a polyaxial bone screw device, for use in an orthopedic surgical procedure, according to the present invention.

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone, or A and B in combination. The expression "A, B and/or C" is intended to mean: A alone, B alone, C alone, A and B in combination, A and C in combination, B and C in combination, or A, B, and C in combination.

The term "allograft and/or autograft bone material" as used herein is broadly defined as bone tissue that is harvested from another individual (allograft), and/or the same individual (autograft) of the same species. Allograft and/or autograft tissue may be used in its native state, or modified to address the needs of a wide variety of orthopedic procedures. The vast majority of allograft and/or autograft bone tissue is derived from deceased donors (cadaver bone). Bone is about 70% mineral by weight. The remaining 30% is collagen and non-collagenous proteins (including bone morphogenic proteins, BMPs). Allograft bone that has been cleaned and prepared for grafting provides a support matrix to conduct bone growth, but is not able to provide growth factors that induce the patient's biology to form bone cells and create new bone tissue. In a preferred embodiment, allograft bone is cleaned, sanitized, and inactivated for viral transmission.

The term "cancellous bone" refers to the medullary portion of bone, devoid of hematogenous and other cellular material. When compared to cortical bone (defined below) cancellous bone is less dense, less stiff, softer, weaker, and more porous. Cancellous bone is also called trabecular bone or spongy bone. Cancellous bone is generally derived from human or animal cadavers.

The term "cortical bone", also known as "compact bone", generally comprises the dense, outer surface of bones that forms a protective layer around the internal bone tissue (such as internal cancellous bone). Cortical bone is harder, stronger, stiffer, and more dense than other forms of bone.

The term "antibiotic" is art recognized and includes antimicrobial agents synthesized by an organism in nature and isolated from this natural source, and chemically synthesized drugs. The term broadly includes but is not limited to: polyether ionophores such as monensin and nigericin; macrolide antibiotics such as erythromycin and tylosin; aminoglycoside antibiotics such as streptomycin and kanamycin; .beta.-lactam antibiotics (having a .beta. lactam ring) such as penicillin and cephalosporin; and polypeptide antibiotics such as subtilisin and neosporin. Semi-synthetic derivatives of antibiotics, and antibiotics produced by chemical methods are also encompassed by this term. Chemically derived antimicrobial agents such as isoniazid, trimethoprim, quinolones, fluoroquinolones and sulfa drugs are considered antibacterial drugs, and the term antibiotic includes these. It is within the scope of the present invention to include compounds derived from natural products, and compounds that are chemically synthesized. The term "antibiotic" as used herein includes those antimicrobial agents approved for human use.

The terms: "polyaxial bone screw", "polyaxial screw", and "bone screw" all refer broadly to a device (a screw) with a hemispherical drive head that can be rotatably-mounted in a connecting member comprising a U-shaped channel sized for rigidly holding a rod with a set-screw. The connecting member is thereby allowed to freely rotate to accommodate a wide range of angles between the rod's axis and the screw's axis. The hemispherical drive head of a polyaxial screw can be mounted in the rod-connecting member such that the screw's orientation can be adjusted angularly with respect to the connecting member, and then locked into place. Polyaxial screws that do not have hemispherical heads are also known.

The term "polyaxial head" as used herein is broadly intended to encompass all screw heads having connecting members that have some ability to toggle or pivot in one or more directions about a center of rotation.

The term "cannulated portion" or "cannulation" broadly means a hollow cavity, hole, bore, reservoir, or other type of hollow, internal volume or space (not necessarily cylindrical in shape) disposed inside at least part of the orthopedic device or implant (e.g., pedicle screw, rod, plate, interbody, etc.). For example, a cannulation may consist of a central bore beginning at or near one end of a pedicle screw and extending longitudinally along the central axis of the screw. Other configurations are possible, however, and the cannulation need not be restricted to having a cylindrical shape or a circular cross-section.

A cannulation may extend throughout the entire length of the orthopedic device, thus creating openings at each end of the device or implant. Alternatively, a cannulation may extend only partially into the interior of the device. The shape and size of the cannulated cavity (e.g., a diameter) may be suitably chosen to allow delivery of the desired substance, through connected fenestrations in the device, to the adjacent bone area of interest. When it is desired to use a cannulated portion of the device as a storage volume or reservoir for holding the substance to be delivered, a cannulation can be made as large as possible, just so long as the device maintains the minimum structural integrity needed for stabilizing the unstable bony structures.

The term "cannulated screw" is defined as a screw with a hollow shaft, and which is suitable for using with a Kirscher wire (e.g., K-wire).

The term "cancellous screw" is defined as a screw with a relatively coarser thread, as compared to a cortical screw, and which is designed to anchor in softer, medullary bone; and which often has a smooth, unthreaded upper portion closer to the screw's head, which allows it to act as a lag screw.

The term "cortical screw" is defined as a screw with a relatively fine thread (as compared to a cancellous screw), which is designed to anchor into denser and harder cortical bone.

The term "fenestration" is defined broadly as any slot, hole, via, penetration, gap, perforation, etc. that defines a fluidic opening, passageway, channel, connection, etc. between the cannulated portion, region, or zone of the device and the outside/exterior surface of the device. Thus, for example, a fenestrated screw comprises an opening or penetration through the screw's shaft that defines a substance-delivering, fluidic pathway between an internal cannulation and the exterior surface of the screw. Fenestrations will typically extend in the radial direction from the internal cannulation to the exterior of the screw or implant, but other configurations are possible. Such fenestrations are separate and distinct from an opening at or near the end of the device or implant created by an intersection of the cannulation with the device's outer surface. Further, in accordance with the present invention, fenestrations may have any necessary shape or size desired to effect the desired delivery of the desired substance. For example, fenestration cross-sections may be round, oval, or square; and may also have a non-uniform cross-section that changes along the fenestration's length (e.g., a tapered channel).

The term "fenestration" includes "microholes" (which can be empty, or can be bone-filled).

The term "fenestration" is also broadly defined herein to include structures and materials that have interconnected porosity; e.g., in a porous, reticulated, "foam-like" material (e.g., partially-sintered porous metal; CVD porous metals and metal alloys; reticulated graphite; and porous ceramics (aluminum oxide, silicon nitride, silicon carbide). The network of interconnected pores in these porous materials can be used to replace drilled microholes (fenestrations) for providing a substance-delivering, fluidic pathway between a cannulated storage region inside the device and the outer surface of the device.

The term "stem cell" broadly refers to any cells that have the ability to divide for indefinite periods of time and to give rise to specialized cells. Stem cells emanate from all germinal layers (ectoderm, mesoderm and endoderm). Typical sources of stem cells include embryos, bone marrow, peripheral blood, umbilical cord blood, and placental blood. Stem cells can be pluripotent, meaning that they are capable of generating most tissue on an organism. For example, pluripotent stem cells can give rise to cells of the skin, liver, blood, muscle, bone.

The term "composite" broadly includes laminated materials that have a laminated or multi-layered type of construction; for example, a structure that is made up of alternating layers of different materials (e.g., bone as layer #1, and metal as layer #2, and bone as layer #3, etc.).

The term "orthopedic device" and "device" is broadly defined herein to include composite orthopedic fixation devices, fasteners, and implants (e.g., bone+metal composite devices).

The words "may" and "can" are used interchangeably herein. For example, the phrase: "the metal or metal alloy may be titanium alloy" is equivalent to the phrase: "the metal or metal alloy can be titanium alloy."

Devices

Certain embodiments are disclosed herein, according to the present invention, that provide innovative orthopedic devices and implants that facilitate, for example, improved spine stabilization, such as: bone screws (e.g., pedicle screws), rods, cross-links, plates, set-screws, spinal interbody spacers, and corpectomy cages. They are designed to provide sufficient strength and load carrying capabilities, while also enhancing bio-integration of the devices with the surrounding bone tissue.

While the devices will be described as, and may generally be used in, the spine (for example, in the lumbar, thoracic or cervical regions), those skilled in the art will appreciate that these devices may be used in other bony parts of the body such as, for example: joints, long bones, or bones in the hand, face, feet, extremities, cranium, bony plates for fracture or tumor throughout the body; and hip/knee/ankle/extremity arm or leg screws/rods/plates, etc. The devices may be designed in different lengths and proportions; and can be used in cervical, thoracic, lumbar, sacral, occipital, extremity and orthopedic surgery. The devices may additionally incorporate optional attachments to robotic members that can provide high (3-D) spatial coordinate resolution via robot-guided tracking of, e.g., pedicle screw placement (e.g., Mazor Robotics Renaissance™ hexapod coordinate tracking tool) and/or direct insertion and placement via robotic tools, such as the Da Vinci® robotic arms.

The orthopedic devices of the present invention may be made from biologically-compatible materials (e.g., medical-grade stainless steel, titanium alloy, or other metals; polymers, such as PEEK, polyurethane, silicon, polylactic acid (PLA), polyglycolic acid (PLGA); or other polymeric materials; ceramics; other materials that are exogenous, some materials derived from animals (e.g., naturally occurring or chemically-modified molecules such as collagen, hyaluronic acid, proteins, carbohydrates, and others); human donor tissues (e.g., "allograft" such as whole organs; tissues such as bone grafts, skin grafts, and others); or from the patients themselves (e.g., "autografts").

Additionally, embodiments using carbon/graphite fiber reinforcement technology (including nanofiber/nanorod/whisker/graphene sheet technology) may completely replace, or, be used along with, the metal or metal alloy components/layers (e.g., titanium component).

In some embodiments of the present invention, the orthopedic device is constructed as a composite structure made of at least two different types of materials: (1) a rigid or semi-rigid load-bearing material (e.g., metal, ceramic, ceramic-metal composite, or a fiber-reinforced material, such as graphite fiber reinforced plastic, carbon-fiber composite, SiC-fiber reinforced SiC, etc.)), and (2) a more compliant (less rigid) material (e.g., polymer, allograft or autograft bone, which can be cancellous or cortical bone, graphite or carbon).

In some embodiments, the orthopedic device may be constructed as a multi-layered composite configuration comprising a core and two surrounding layers (middle and outer layers); wherein the core is a more compliant (less rigid) material (e.g., allograft and/or autograft bone), the middle layer is a rigid or semi-rigid load-bearing material (e.g., a metal or metal alloy), and the outer layer is a more compliant (less rigid) material (e.g., allograft and/or autograft bone. In some of these embodiments, the composite configuration may comprise about 50% allograft and/or autograft bone, and about 50% metal or metal alloy. In other embodiments, each layer (core, middle, and outer) has approximately the same thickness as the other two layers (i.e., 33%, 33%, 33%). In other embodiments, the thickness of the different layers can be chosen to be any thickness that provides the necessary and/or optimum properties for a specific design. In other embodiments, the "metal or metal alloy" may comprise a titanium alloy, cobalt-chromium alloy, niobium alloy, tantalum alloy, or a stainless steel alloy. In another embodiment, the titanium or metal parts are replaced with carbon or graphite fiber reinforced parts in similar ratios as described above with the titanium embodiment.

In some embodiments, the outermost bone layer comprises a thin shell of allograft/autograft bone that has been micro-machined to closely fit the outer contours and surface of the middle metal layer; in which case the thin shell of bone is glued onto the metal substrate, or attached some other way. Alternatively, a mixture comprising primarily ground up particles of allograft/autograft bone and a biologically-acceptable binder material is sprayed onto the metal substrate (preferably with a roughened metal surface), followed by baking and curing to remove the volatile binder, thereby leaving an essentially 100% pure, nearly fully-dense allograft/autograft outermost bone layer.

In some embodiments, the inside and/or outside surfaces of the metal structural layer (e.g., titanium alloy) can comprise a nano-textured or nano-porous surface layer or coating, which enhances bonding, bond strength, and bond fatigue life by providing an extended surface area for mechanical interlocking, enhanced chemical reactivity, and reduced stresses across a graded interlayer. This can be accomplished, for example, by electrospinning a very thin, titanium-oxide based, ceramic nanowire scaffolding (nano-porous layer) on a titanium substrate. This has been demonstrated for hip replacement, dental reconstruction/implants, and vascular stenting. Such a surface treatment can increase attachment of the orthopedic device to the surrounding bone, and increase pullout strength.

In other embodiments of the present invention, the orthopedic device is constructed as a skeleton structure that is only made of the rigid or semi-rigid load-bearing material (e.g., metal, ceramic, ceramic-metal composite). Then, at some time either (a) before the device is surgically implanted, or (b) after the device has been implanted, but still during surgery, the empty/open cannulation(s) and/or the fenestrations inside of the device's skeleton structure are filled (infiltrated) with a liquid or gel-like "bone growth cocktail" or "Liquid Bone". In some embodiments, a bone growth cocktail can comprise a mixture of: (a) stem cells, (b) small particles/powder/chips of allograft and/or autograft bone, (c) one or more bone growth factors/adjuncts/stimulants, such as BMP's (bone morphogenic proteins, e.g., BMP-2 (except not for the anterior cervical spine as BMP-2 is contraindicated)) and/or (d) a demineralized bone matrix or bone chips substrates composed of cadaveric allograft material with stem cells, which will transform into solid, living bone tissue (after having been implanted inside of a patient's body).

In other embodiments, such a bone growth cocktail mixture can additionally, or optionally, comprise an efficacious dose of Teriparatide (Forteo™, made by Eli Lilly, Inc.), which is a recombinant human version, rDNA, of a portion (amino acid sequences 1-34), of the full human parathyroid hormone, PTH, which contains 84 amino acids. When used for the FDA-approved method of treating osteoporosis, once-daily injections of teriparatide has been found to activate osteoblasts more than osteoclasts, and thus has a net effect of stimulating new bone formation leading to increased bone mineral density. Additional testing would be needed, however, to demonstrate the usefulness of constant (i.e., non-intermittent) exposure of a bone graft site or bone fusion site to Teriparatide (PTH 1-34).

The bone growth source mixture comprising stem cells, small particles of allograft and/or autograft bone, bone growth factors, etc. migrates from the cannulation (storage reservoir) and flows (diffuse) radially outwards through the fenestrations. Upon exiting the fenestrations, they can deposit locally and/or disperse and migrate or flow across the exterior surface of the device, eventually depositing on the device's surface. Then, given the proper environmental conditions, a thin layer of living bone tissue begins to grow, and eventually forms a continuous, consolidated layer (coating) of solid, living bone tissue. The layer of living bone can be, for example, 1-2 mm thick, and it can infiltrate and bond to the patient's pre-existing bone structure (e.g., a vertebra bone), thereby enhancing the bio-integration of the orthopedic device with the patient's own bony structures. The outer layer of bone is attached, in part, to the central core of bone via the bony limbs inside of the fenestrations that connect those layers.

In some embodiments, the exterior surface of the device (pedicle screw, rod, plate, etc.) can have a roughened or pitted surface (chemically or mechanically etched or pitted) to provide an enhanced/extended surface area for locking-onto the coating of living bone tissue. Optionally, the roughened surface can be pre-coated (before the device is surgically implanted) with a nano-thin or micro-thin layer of apatite or hydroxyapatite bone-like material to provide a precursor/prepared surface that helps bone growth and subsequently enhances bonding and bio-integration of the device.

In some embodiments, the cannulated portion(s) of the device can be pre-filled with the bone cocktail mixture and stored in a frozen state prior to use.

In some embodiments, the bone cocktail mixture can additionally comprise silver nanoparticles, which provide additional antibiotic capability.

In one of the embodiments presented above, the orthopedic device is implanted during surgery as an empty skeleton structure, i.e., without any bone tissue inside. Then, after implantation, but still during surgery, a bolus of the liquid or gel-like bone cocktail mixture is loaded/injected into the device's cannulation(s) of the device. Then, over a period of time, the bone mixture migrates/diffuses outwards through a series of fenestrations (that fluidically connect the inner cannulation to the outer surface of the device) and onto the surface of the device (as described previously).

Figure 13A:
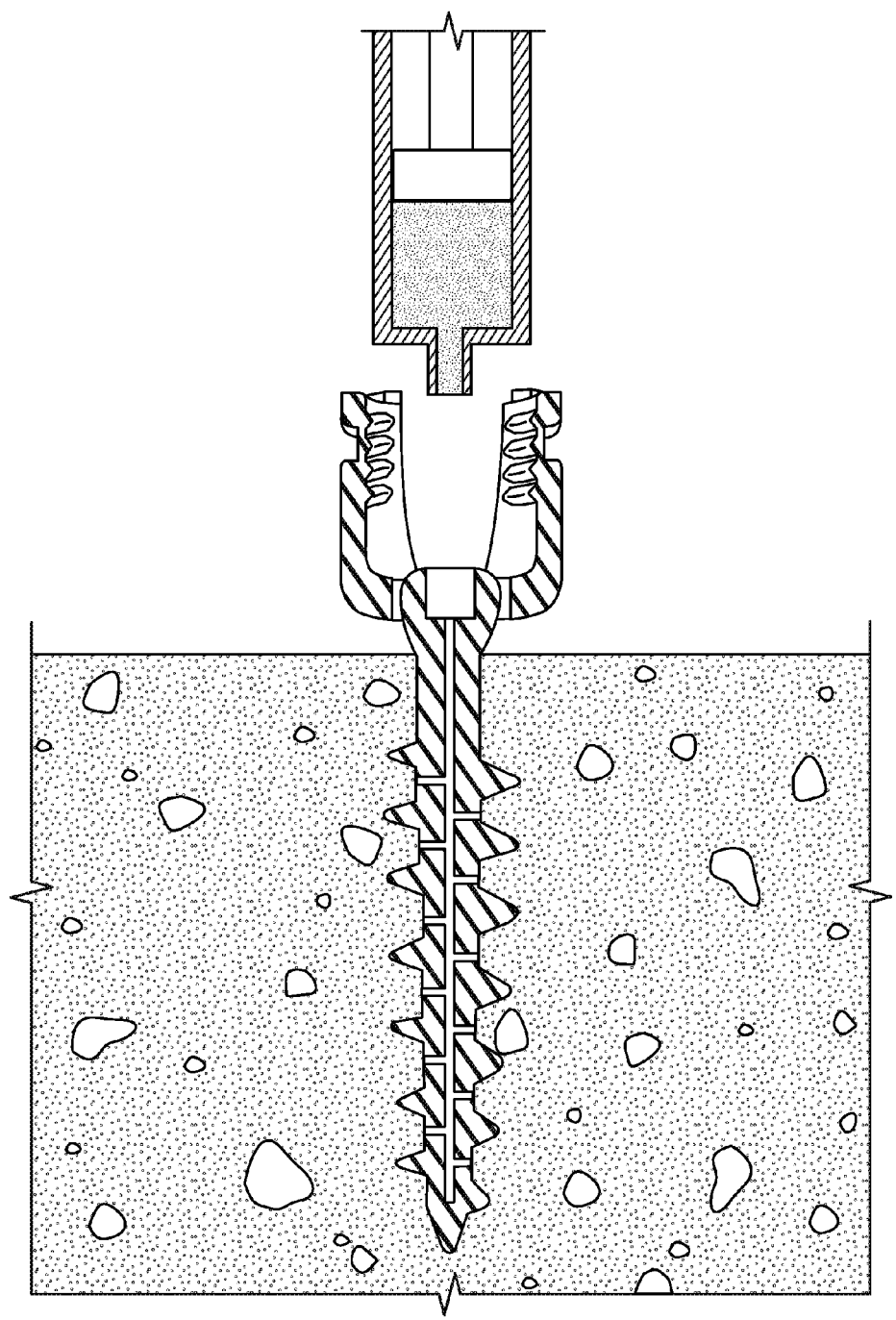
FIG. 13A shows the embodiment of FIG. 1 receiving a syringe for injecting a bone growth mixture.
Figure 13B:
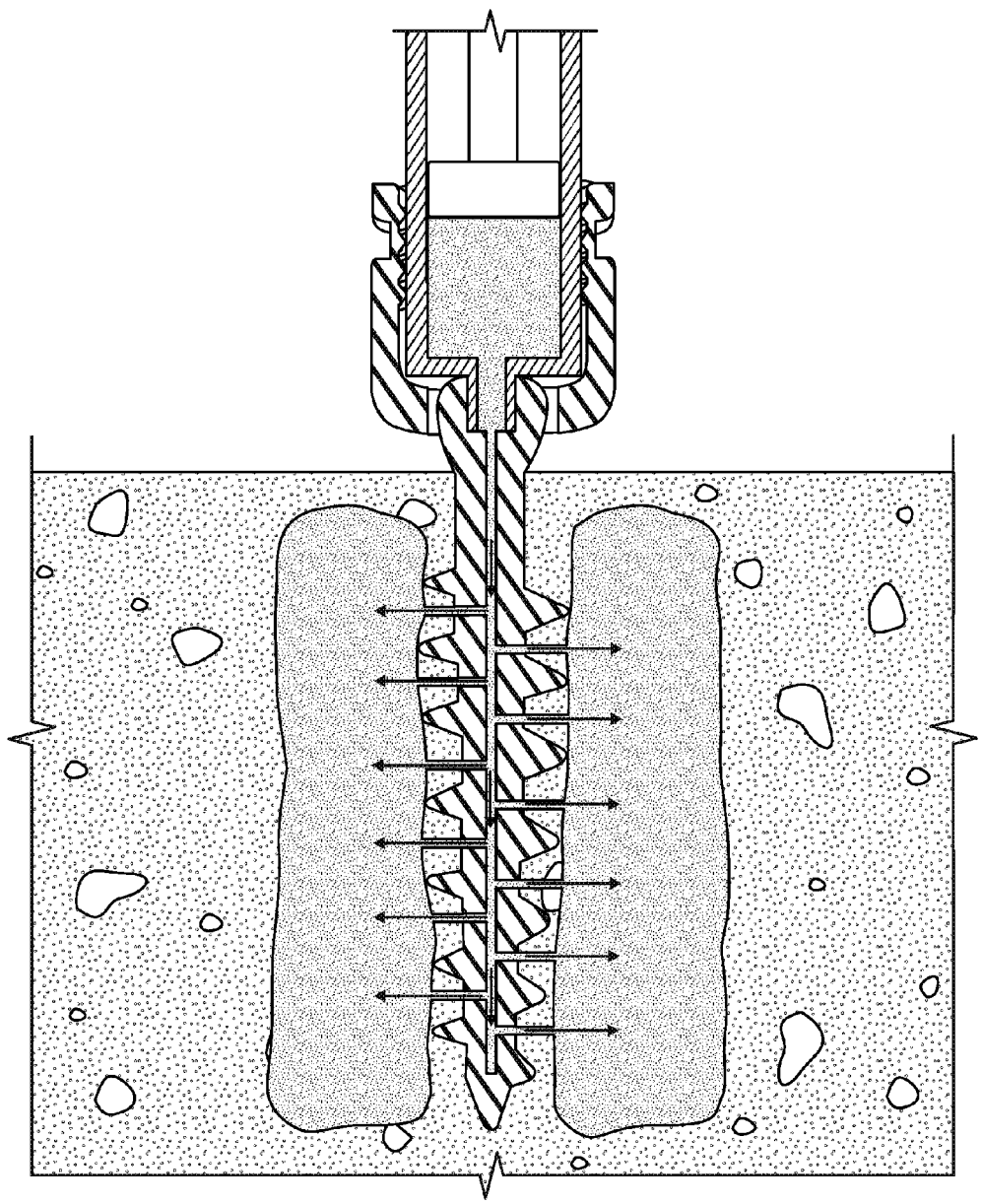
FIG. 13B illustrates the injection of a bone growth mixture in accordance with the present invention.

Furthermore, as shown in FIGS. 13A and 13B, the bone cocktail mixture can be initially injected by applying a high pressure and forcing the mixture under pressure to flow more rapidly through the fenestrations and out into the surrounding tissue of the patient's body for some distance (e.g., few mm's). If the device has been implanted into a bony structure (e.g., a pedicle of a vertebra), then the surrounding tissue can comprise porous, cancellous bone. In this case, the bone cocktail mixture will infiltrate into the surrounding porous, cancellous bone (which could include damaged or diseased bone tissue), thereby strengthening and enhancing the bio-integration of the implanted device with the surrounding bony structure when the bone cocktail transforms into solid, living bone tissue. In embodiments where the implanted device is a bone screw, then using this method of forcing the bone cocktail mixture to infiltrate and reinforce the surrounding bone will result in increased pullout strength of the bone screw in the pedicle.

The method described above of applying a high pressure (e.g., by using a syringe with a tip mechanically coupled to an open end of a cannulation) and forcing the mixture to flow more rapidly under pressure through the fenestrations and out into the surrounding tissue of the patient's body for some distance, can be applied to any of the composite orthopedic devices described in the present specification, including, but not limited to: bone screws, plates, rods, bars, crosslinks, discs, tubes, cylinders, set screws, interbody spacers, and corpectomy cages. This method can be used before, or after, or both before and after, the orthopedic device has been surgically implanted.

In some embodiments, a polyaxial bone screw that is devoid of any bone tissue (i.e., an empty skeleton structure) would be similar to a "cannulated screw" (which has a full-length cannulation that makes it suitable for using with a Kirscher wire (e.g., K-wire)), which has been modified by the addition of fenestrations (holes) that connect the surface to the cannulation. However, it might be necessary to insert a plug (not illustrated) to block the exit end of the cannulation 20 at the distal end 16 of the screw (See FIG. 1). Plugging the distal end of the cannulation 20 would prevent any undesirable loss of bone growth cocktail flowing out the distal end 16, especially if the bone cocktail is being injected into the cannulation 20 to force it to flow outwards through the radial fenestrations 20.

All surfaces of the different components and parts of a composite orthopedic device, according to the present invention, can be coated with an antibiotic solution, including, but not limited to: any titanium or other metal parts, including the inside of any cannulations or fenestrations.

In some embodiments, the orthopedic devices of the present invention can provide radiofrequency (RF) stimulation capability by incorporating bioengineered, RF-activated implants inside of the orthopedic device, which is capable of responding to external sources of RF stimulation and stimulating activity of the associated implant in order to increase bone fusion and prevent pseudoarthrosis and implant failure, and neurologic injury and re-operation. These RF-activated implants can also stimulate areas outside of the implanted device, such as the surrounding patient bone, to stimulate fusion bone growth in that surrounding area. In some embodiments, the entire composite orthopedic device has RF-activating capacity. In other embodiments, only part of the orthopedic device has RF-activating capacity (e.g., such as a special insert of RF-receiving material implanted inside of, or attached to the surface of, the composite orthopedic device). RF-receiving material that can be used as an RF-activating implant include (1) a conducting antenna structure capable of receiving RF-radiation, and (2) materials (e.g., polymers, water-containing materials, hydrated-materials) that have a high polar-moment, capable of being rapidly and efficiently heated by RF microwave radiation.

Previously, an embodiment was disclosed that included the rDNA hormone, Forteo™ (Teriparatide, PTH 1-34), in a bone growth cocktail. To achieve an optimum effect on bone growth, however, the hormone should ideally be "injected" once a day; in an intermittent fashion. In one embodiment, the composite orthopedic device comprises Externally-Activated (EA) means for releasing a fixed volume of a liquid (i.e., Forteo™ either alone, or combined with the bone growth cocktail mixture), from an internal storage reservoir (i.e., a cannulation), where it is pumped or otherwise moves/migrates away from the implanted device and is delivered/deposited to a region where bone growth (preferably enhanced growth) is desired. The external activation (EA) can be due to exposing the body with the implant to a localized source of RF-radiation, a localized magnetic field (pulsed or steady), or a combination of both. Inside of the orthopedic device, a MEMS-type micro-valve (connected to the cannulation) can control the flow of liquid Forteo™ and/or bone growth cocktail, and can open or close upon being exposed to the RF-radiation or magnetic field. Another mechanism for causing a micro-valve to open/close is a local temperature rise due to localized heating from RF-radiation (e.g., microwave radiation).

In preferred embodiments of the present invention, the composite orthopedic devices comprise one or more cannulations (storage reservoirs) connected to the exterior surface of the device via one or more fenestrations. In general, unless otherwise specified, the orthopedic device comprises a sufficient number and spacing of fenestrations and a sufficient number and volume of cannulations to supply a bone growth cocktail mixture to all exposed, exterior surfaces of the device. However, in specific applications, it may be undesirable to have an outer layer of bone covering the internal, structural layer of the device (e.g., a titanium layer). For example, in order to preserve zero-profile (zero-P) sidewall surfaces of an interbody spacer, it would be undesirable to include fenestrations in those sidewall sections. Or, where metal-to-metal contact needs to be made between mating surfaces (e.g., in a corpectomy cage) no fenestrations would be included that penetrate those particular mating surfaces.

In some embodiments, fenestrations are 1-2 mm in diameter, and are spaced apart a distance of 2-5 mm. These holes can be drilled with a traditional drill. Alternatively, or additionally, a high-powered laser or water-jet machine can be used to drill 100's to 1000's of these types of microholes using robotic technology, which can have the same or much smaller diameter; and that can have the same or much smaller spacing between holes, if needed. Decreasing the spacing between fenestrations (while increasing the number of fenestrations) can reduce potentially undesirable variations in the thickness of the outer bone layer from hole to hole.

Examples of Composite Orthopedic Devices

FIGS. 1-12 show examples of various embodiments of composite orthopedic devices, according to the present invention. Examples of composite devices that are illustrated include: a polyaxial bone screw, a rod, a 4-screw spinal fusion construct, a thick plate, a bar, and an expandable corpectomy tube cage. Other devices, which are not illustrated, are covered by the methods and designs of the present invention, including: a composite set screw, a composite crosslink, and a composite spinal fusion interbody spacer (with or without angled screw holes).

Figure 2:
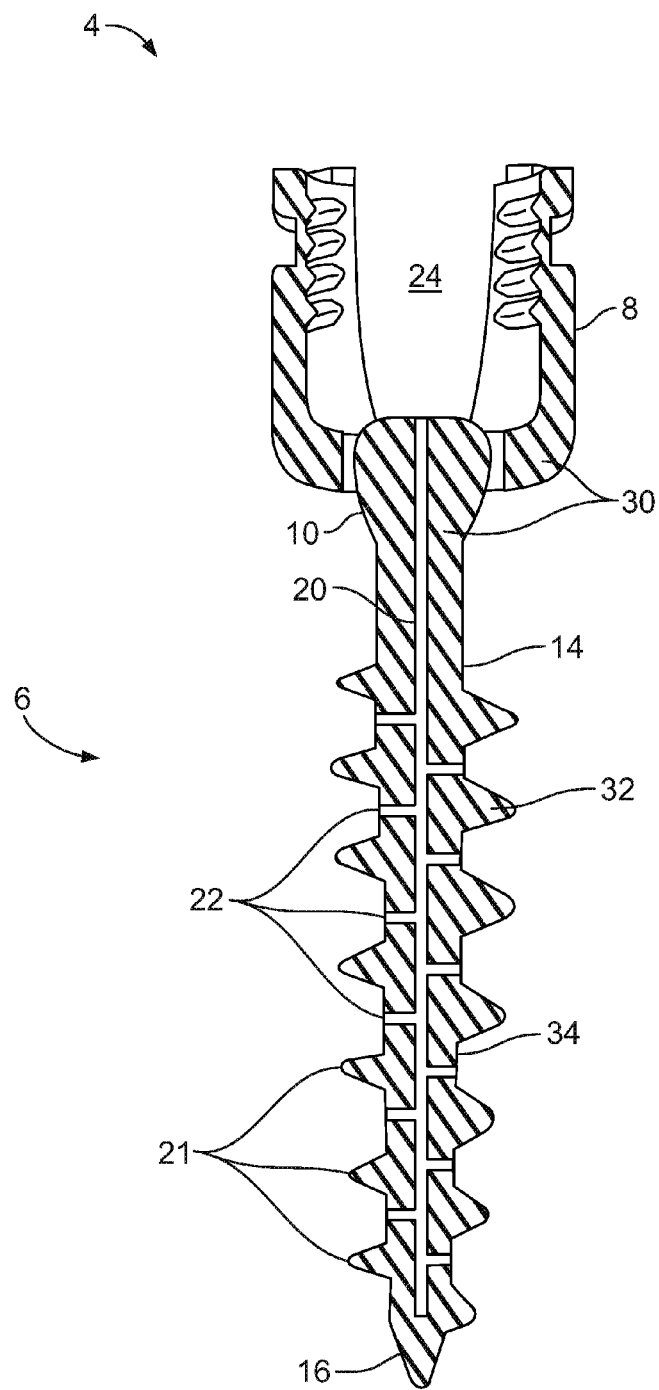
FIG. 2 is a cross-section view along the screw's central axis, of the example of a polyaxial bone screw device shown in FIG. 1.

FIG. 1 shows an isometric side view of an example of a polyaxial bone screw device for use in an orthopedic surgical procedure, according to the present invention. Polyaxial bone screw device 4 comprises a bone screw 6 rotatably attached to rod-connecting member 8 (i.e., rod-connector 8). Bone screw 6 (e.g., a pedicle screw) comprises a hemi- or semi-spherical polyaxial drive head 10 and a body 12. The polyaxial drive head 10 functions as a ball-and-socket joint housed inside of the base of rod-connector 8. This configuration gives bone screw 6 the ability to rotate (swivel) close to +/−90°, polyaxially (i.e., 360° relative to the central axis of rod-connecting member 8), as limited by the shape of the polyaxial drive head (10) and on how it blends/tapers into rod-connector 8. Screw body 12 has a distal tip 16; and an outwardly cylindrical threaded shaft 14 extending from the drive head 10 to the tip 16; wherein the shaft 14 comprises a cannulation 20 (as illustrated in FIG. 2) extending along the screw's central axis from the drive head 10 along at least a portion of the length of the shaft 14. Screw shaft 14 comprises a plurality of radial fenestrations 22 that fluidically connect cannulation 20 to the exterior surface 18 of shaft 14.

Still referring to FIG. 1, shaft 14 comprises helical screw threads 21 from the vicinity of drive head 10 to distal tip 16. Shaft 14 tapers outwardly adjacent to the drive head 10 to form a tapered undercut for the drive head. In another embodiment, fenestrations 22 are spaced apart axially so as to occur every two full rotations of the threaded shaft. Fenestrations 22 can be cylindrical, with a diameter of about 2 mm. In another embodiment, each fenestration has a square cross-section that is about 2 mm in width and height.

Bone screws, according to the present invention, such as the example illustrated in FIGS. 1 and 2, are made of a composite material comprising at least one layer of allograft and/or autograft bone, and at least one layer of a metal or metal alloy.

FIG. 2 shows a cross-section view cut along the screw's central axis of the polyaxial bone screw device 4 previously shown in FIG. 1. Bone screw 6 is made of a multi-layered composite material comprising a central core 30, surrounded by two layers (32 and 34); wherein the core 30 is made of allograft and/or autograft bone, the middle layer 32 is made of a metal or metal alloy, and the outermost layer 34 is made of allograft and/or autograft bone. In certain embodiments, the overall composition of the bone screw is about 50% allograft and/or autograft bone and about 50% metal or metal alloy. In some embodiments, each layer (core 30, middle 32, and outer 34) has approximately the same radial thickness (i.e., ⅓, ⅓, ⅓). The metal or metal alloy used for the middle layer 32, and the screw threads, may be titanium, titanium alloy, cobalt-chromium alloy, niobium alloy, tantalum alloy, or stainless steel. The allograft and/or autograft bone used in central core 30 and outer layer 34 may comprise cancellous bone, cortical bone, or a combination of both cancellous and cortical bone. In some embodiments, bone screw 6 has a torque shear strength of at least 0.10-0.20 Newton-Meters. In another embodiment, bone screw 6 has a pullout force of at least 500-700 Newtons. In another embodiment, the titanium or metal parts are replaced with carbon or graphite fiber reinforced parts in similar ratios as described above with the titanium embodiment.

Referring still to FIG. 2, in one embodiment, the composite bone screw is coated with an antibiotic solution. In another embodiment, the cannulated portion 20 of shaft 14 is filled with stem cells. In another embodiment, the cannulated portion 20 of shaft 14 is filled with allograft and/or autograft and/or autograft bone. In another embodiment, the cannulated portion 20 of shaft 14 is filled with one or more bone growth factors, such as BMP-2. In another embodiment, the cannulated portion 20 of shaft 14 is filled with a combination of stem cells, allograft and/or autograft and/or autograft bone, and one or more bone growth factors, such as BMP-2.

Figure 3:
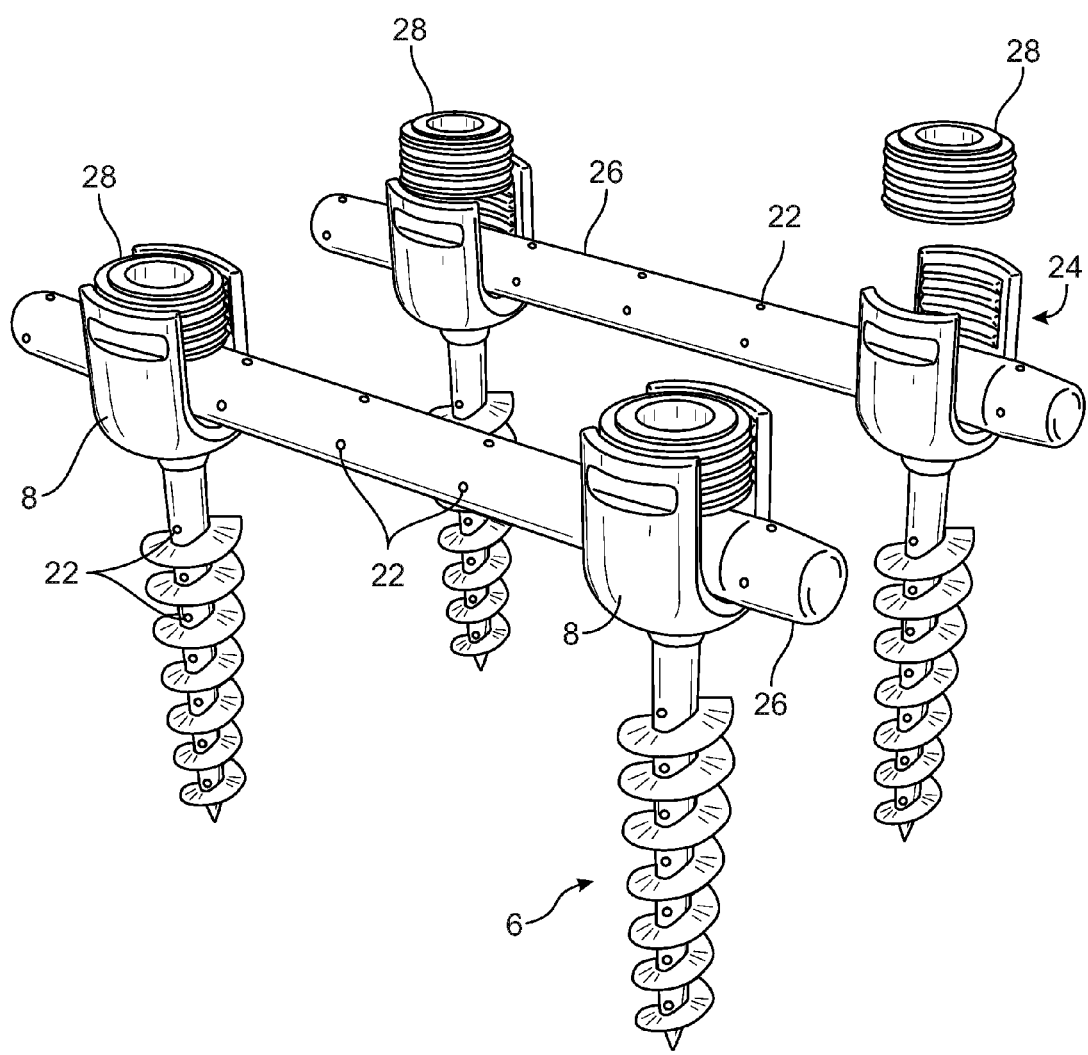
FIG. 3 is an isometric view of an embodiment of a rod for use in a surgical procedure featuring fasteners for attaching the rod to a pair of bone screws.

FIG. 3 shows an isometric view of a spine stabilization assembly (e.g., for stabilizing lumbar vertebra L4/L5), according to the present invention. The assembly comprises a pair of composite rods 26, with each rod 26 being connected to a pair of composite bone screws 6 (e.g, pedicle screws). Each rod 26 is positioned in the U-shaped channel/opening 24 of rod-connecting member 8, and secured with one (or more) set-screws 28. Set-screw 28 is threadedly disposed within the rod-connecting member 8, and is operable for compressing the rod 26 against the top of screw head 10, thereby rigidly securing the rod in place. Multiple examples of fenestrations 22 can be seen in FIG. 3.

In various embodiments, set-screw 28 may be constructed of a composite material comprising a core and two layers; wherein the core is allograft and/or autograft bone, the middle layer is a metal or metal alloy, and the outermost layer is allograft and/or autograft bone. In certain embodiments, the set screw may be constructed of a material comprising about 50% allograft and/or autograft bone and about 50% metal or metal alloy. In various embodiments, the metal or metal alloy may be titanium, cobalt-chromium, niobium alloy, and tantalum alloy. The allograft and/or autograft and/or autograft bone may be cancellous or cortical bone. In another embodiment, the set screw is coated with an antibiotic solution. In another embodiment, the titanium or metal parts are replaced with carbon or graphite fiber reinforced parts in similar ratios as described above with the titanium embodiment.

FIG. 4A shows a cross-section view cut along the length of a composite rod for use in an orthopedic surgical procedure, according to the present invention. Rod 26 comprises a shaft 36 having a proximal first end 37 and a distal second end 39, wherein the shaft 36 comprises a cannulation 38 extending along at least a portion of the axial length of the shaft; wherein the cannulated length 38 of the shaft contains at least one radial fenestration 40; wherein the rod 26 is constructed of a composite multi-layered material comprising allograft and/or autograft and/or autograft bone, and a metal or metal alloy. In this example, cannulation 38 extends along the entire length of rod 26, and intersects the distal second end 39 of shaft 36; wherein the intersection defines opening 41 at the distal end of cannulation 38. Opening 41 can be used to access the cavity (hollow space) of cannulation 38 and fill the cavity with stem cells and other bone growth material, such as a bone cocktail precursor mixture. After filling the cannulation 38 with the bone precursor mixture, then opening 41 can be plugged or otherwise closed, if needed. Optionally, the filling of cannulation 38 can be performed with sufficient pressure to also completely prefill the radial fenestrations 40 with the bone precursor mixture.

Referring still to FIG. 4A, the composite orthopedic rod 26 may be constructed of a multilayered composite material comprising a core and two layers; wherein the core 42 is allograft and/or autograft and/or autograft bone, the middle layer 44 is a metal or metal alloy, and the outermost layer 46 is allograft and/or autograft and/or autograft bone. In certain embodiments, the composite rod may be constructed of a material comprising about 50% allograft and/or autograft and/or autograft bone and about 50% metal or metal alloy. In some embodiments, each layer (core 42, middle 44, and outer 46) has approximately the same radial thickness (i.e., ⅓, ⅓, ⅓). In various embodiments, the metal or metal alloy may be titanium alloy, cobalt-chromium, niobium alloy, and tantalum alloy. In another embodiment, the titanium or metal parts are replaced with carbon or graphite fiber reinforced parts in similar ratios as described above with the titanium embodiment. Still referring to the composite rod, the allograft and/or autograft bone may be cancellous or cortical bone. In another embodiment, the composite rod is coated with an antibiotic solution. In another embodiment, the cannulated portion of the shaft may be filled with stem cells. In various embodiments the cannulated portion of the shaft may be filled with allograft and/or autograft bone.

FIG. 4B shows a cross-section view showing a first plane, A-A, cut perpendicular to the long axis of the rod 26. In this view, the central core 42 (made of bone), the middle layer 44 (made of metal or metal alloy), and the outer layer 46 (made of bone), can be seen as cross-hatched layers.

FIG. 4C shows a cross-section view of a second plane, B-B, cut perpendicular to the long axis of the rod, passing through a set of fenestrations. Cannulation 38 is centered along the central axis of the rod, and is connected to four radial fenestrations 40, which are oriented at every 90° to each other. The cannulation 38 and radial fenestrations 40 are filled with solid bone. The middle layer 44 (made of metal or metal alloy), and the outer layer 46 (made of bone), can be seen. In other embodiments, one or more cannulations (not shown) can be placed off-axis from the rod's central axis. In other embodiments, the rod can be curved (non-straight) to match a patient's specific anatomy.

Figure 5A:
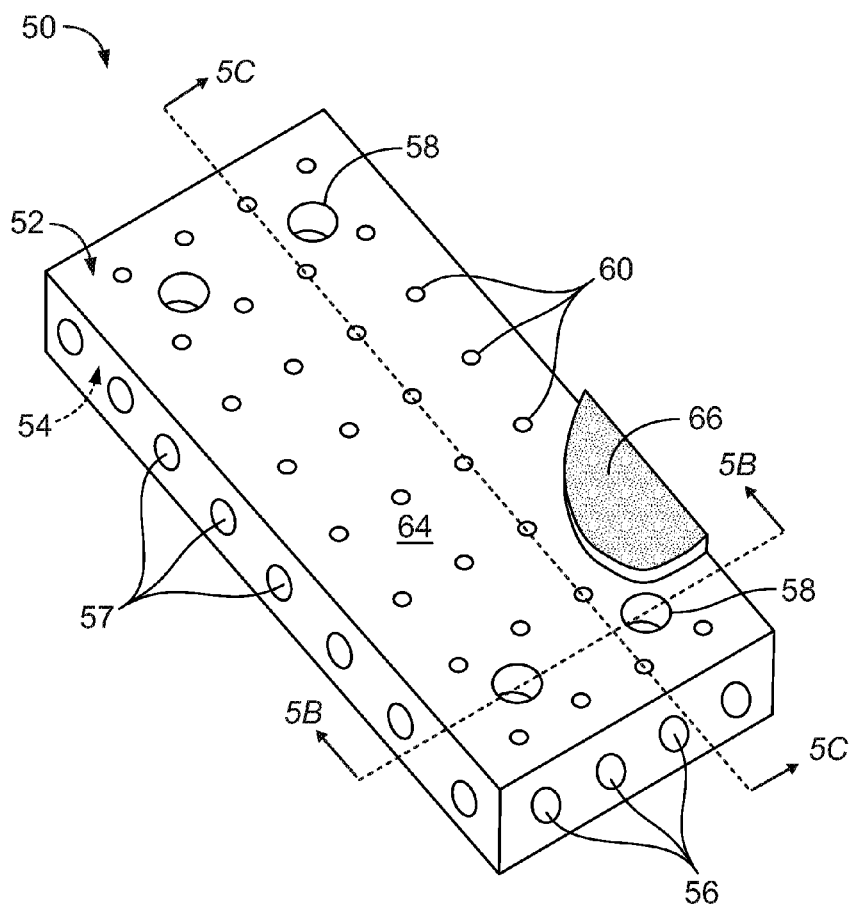
FIG. 5 is a cross-section view of an embodiment of a plate for use in a surgical procedure.

FIG. 5A shows an isometric view of a composite plate for use in an orthopedic surgical procedure, according to the present invention. Plate 50 comprises a main/structural body 64 defining a top side 52, an bottom side 54, a set of four bone screw bore holes 58 (two holes at each end of the plate) configured to cooperate with four corresponding bones screw (not shown) to attach the plate to bony structure(s) within the body; wherein the plate contains a plurality of fenestrations 60 (32 fenestrations in this example), where each fenestration is a small hole that penetrates from the top side 52 down through a cannulation 56 or 57, then passing down and out through the back side 54; and wherein the plate is constructed of a composite material comprising allograft and/or autograft bone and a metal or metal alloy.

Figure 5B:
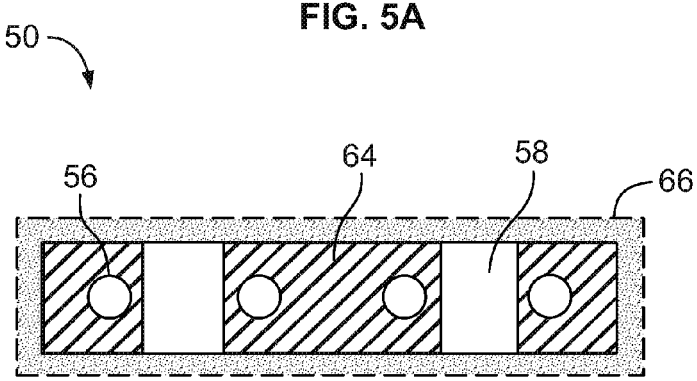
Figure 5C:
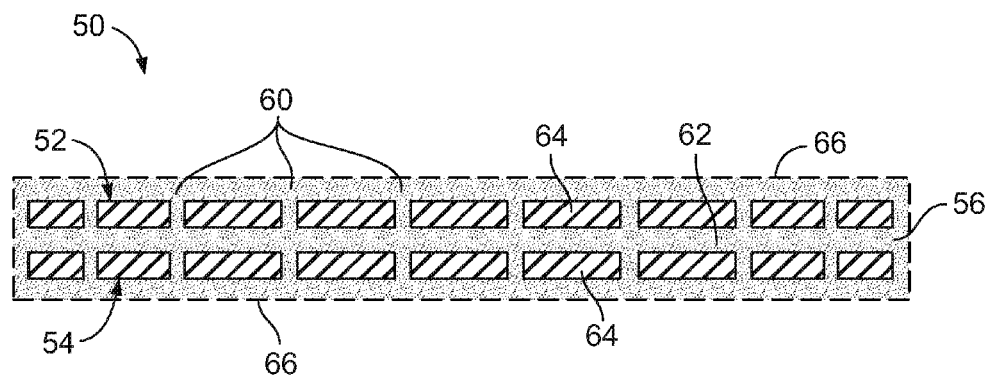

FIGS. 5B and 5C show a pair of cross-section views cut through the composite plate at two different locations, A-A, and B-B, (see FIG. 5A for the location of the cutting planes). In these embodiments, plate 50 comprises multiple layers of different materials, for example: a core layer 62 (see FIG. 5C) and two other layers, 64 and 66; wherein the core layer 62 is allograft and/or autograft bone, the middle layer 64 is a metal or metal alloy, and the outermost layer 66 is allograft and/or autograft bone.

In certain embodiments, the plate may be constructed of a material comprising about 50% allograft and/or autograft bone and about 50% metal or metal alloy. In other embodiments, each layer has approximately the same thickness (e.g., 20%, 20%, 20%, 20%, 20%) since there are a total of 4 layers in a complete plate: i.e., core layer 62, middle layer 64 (top and bottom layers), and outer layer 66 (top and bottom layers) for a total of 5 layers). In various embodiments, the metal or metal alloy may be titanium, titanium alloy, cobalt-chromium alloy, niobium alloy, tantalum alloy, or stainless steel. The allograft and/or autograft bone may be cancellous or cortical bone, or a combination of cancellous and cortical bone. In another embodiment, the titanium or metal parts are replaced with carbon or graphite fiber reinforced parts in similar ratios as described above with the titanium embodiment.

In another embodiment, the plate is coated with an antibiotic solution. In another embodiment, the fenestrations may be filled with stem cells. In various embodiments, the fenestrations may be filled with allograft and/or autograft bone.

Figure 5D:
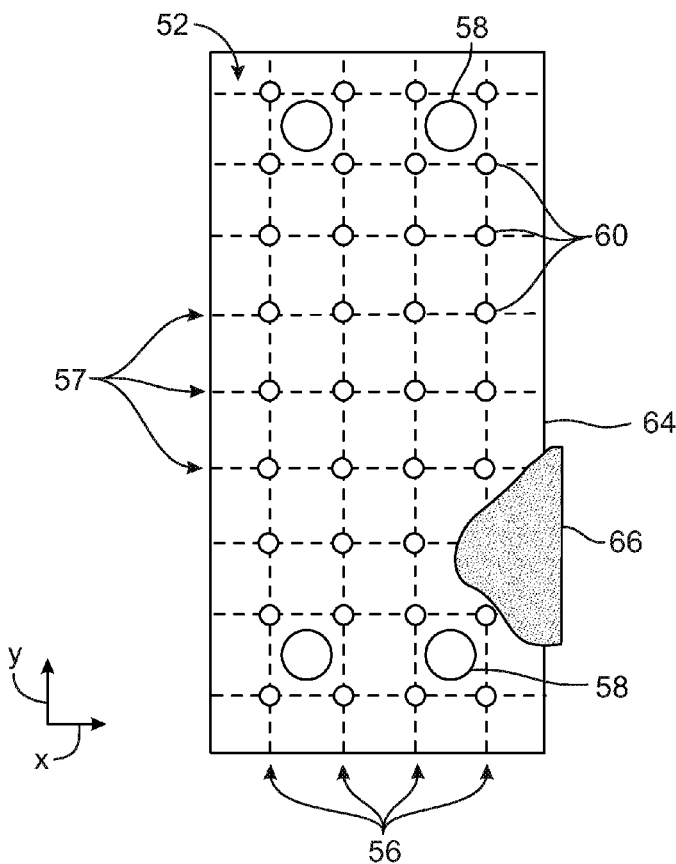

FIG. 5D shows a top view of composite plate 50. In this example, the composite plate has a rectangular shape with an aspect ratio (as viewed from the top, as in FIG. 5D) of about 2 (meaning that the length of the plate is about twice as long as the width of the plate). Other aspect ratios can be used, ranging from square (1:1) to "long and skinny" (e.g., 5:1 to 6:1). A plate with an aspect ratio greater than about 10:1 would be considered a "strip" or a "bar". Plate 50 is illustrated as being a flat plate, however non-flat (curved) plates can be used without departing from the general scope of the invention. Accordingly, in other embodiments, composite plate 50 can be curved (i.e., non-flat) in one, or two, different directions, depending on the needs of a specific patient's anatomy. Likewise, in other embodiments, composite plate 50 can have curved, non-flat sidewalls, with the four sidewalls having the same, or different, curvatures.

Referring to FIGS. 5A through 5D, a number of other features are illustrated. The central core layer 62 of plate 50 comprises a rectangular grid (network) of intersecting cannulations 56 and 57. This is indicated by the orthogonal grid of dashed lines in FIG. 5D, where the dashed lines correspond to the centerline of each cannulation. In this example there are four, parallel cannulations 56 that run the entire length of the plate in a direction parallel to the y-axis (see FIG. 5D). In the other direction, there are eight, parallel cannulations 57 that run the entire width of the plate in a direction parallel to the x-axis (see FIG. 5D). The cannulations in this example are circular holes, and there are a total of twelve (12) cannulations.

FIGS. 5A through 5D show a plurality of fenestrations 60, which penetrate completely through the plate from the top surface 52 to the bottom surface 54, passing through cannulations 56 or 57. In this example, the central core 62 in FIG. 5C is the same feature as cannulation 56. Fenestrations 60 provide a fluidic connection between the cannulations and the exterior surface of the plate. When the cannulations 56 and 57 are filled with a "bone cocktail" mixture of stem cells, particles of bone, bone growth factors, and a liquid or gel-like binder, then the 32 fenestrations 60 provide a pathway for the bone cocktail to migrate from the cannulations to the exterior surface of the plate, whereupon they can flow across the plate's surface to generate full coverage of the surface by the mixture. After some period of time, the bone growth mixture (cocktail) transforms into living bone tissue. The outermost layer 66 of living bone tissue is indicated by the dashed line 66 in FIGS. 5B and 5C. Outer bone layer 66 can be about 1-2 mm thick, in some embodiments. Composite plate 50 can have a greater, or lessor, number of fenestrations that illustrated in this example (which has 32 fenestrations); and the spacing between fenestrations can be adjusted as needed. Likewise, the diameter of each fenestration hole can be greater, or lessor, than about 1-2 mm. Likewise, the diameter of the cannulations, and the spacing between cannulations, can be adjusted as needed. The size and placement of the cannulations are preferably chosen to not intersect with, or otherwise interfere with, the bone screw bore holes 58.

Note that in FIGS. 5A and 5D, only a portion of the outermost layer 66 of bone is illustrated; the remainder of layer 66 has been artificially removed so that the underlying pattern of fenestrations 60 can be easily seen.

In various embodiments, the present invention provides a spinal fusion interbody spacer (not illustrated) comprising: a body having superior and inferior abutment surfaces sized and shaped to be adapted to abut against adjacent spaced vertebrae; and said body having concave lateral side surfaces, wherein the spacer contains a least one fenestration from the inferior surface to the superior surface; and wherein the spacer is constructed of a material comprising allograft and/or autograft bone and a metal or metal alloy.

In another embodiment, the interbody spacer may be constructed of a material comprising a core and two layers; wherein the core is allograft and/or autograft bone, the middle layer is a metal or metal alloy, and the outermost layer is allograft and/or autograft bone. In certain embodiments, the interbody spacer may be constructed of a material comprising about 50% allograft and/or autograft bone and about 50% metal or metal alloy. In various embodiments, the metal or metal alloy may be titanium, cobalt-chromium, niobium alloy, and tantalum alloy. Still referring to the interbody spacer, the allograft and/or autograft bone may be cancellous or cortical bone. In another embodiment, the interbody spacer is coated with an antibiotic solution. In another embodiment, the fenestration may be filled with stem cells. In various embodiments the fenestration may be filled with allograft and/or autograft bone. In another embodiment, the titanium or metal parts are replaced with carbon or graphite fiber reinforced parts in similar ratios as described above with the titanium embodiment.

In some embodiments of cervical interbody spacers, 1-4 screws are angled at roughly 45 degrees for anchoring the interbody spacer directly into the solid end-plates of the adjacent vertebrae above and below. This design can eliminate the need to attach a separate plate to prevent the interbody spacer from accidently being dislodged. Additionally, these types of interbody spacers with the 1-4 angled screw holes can also be used for thoracic and lumbar interbody spacers. Using any type of interbody, it's still highly desirable to implant/install the interbody so that there is less than 0.5 mm (ideally, zero-profile) distance of overhanging material sticking out past the adjoining vertebra (meaning that no component of the interbody is anterior to the anterior aspects of the vertebral bodies). No features of the various embodiments of the present invention should interfere with achieving these goals. However, if excess bone growth of the outermost layer of bone is a concern, e.g., around the circumference of the interbody, then a decision can be made to not include any fenestration holes that penetrate some, or all, of the circumferential sidewalls of the interbody, thereby preventing bone growth on those exterior surfaces (especially the anterior surfaces of the sidewall).

In various embodiments, the present invention provides a composite crosslink member (not illustrated), to add stability to a spinal fusion construct; comprising a composite rod or bar, fitted with attachment means at both ends for rigidly attaching the crosslink laterally between a left side and a right side (i.e., left and right vertically-oriented rods, such as the pair of rods shown in FIG. 3. The crosslink devices can be attached from rod-to-rod, from screw head-to-screw head, or from screw-head to an adjacent rod. The composite crosslink member contains at least one fenestration from the inferior surface to the superior surface; and crosslink member is constructed of a material comprising allograft and/or autograft bone and a metal or metal alloy. In another embodiment, the crosslink member may be constructed of a material comprising a core and two layers; wherein the core is allograft and/or autograft bone, the middle layer is a metal or metal alloy, and the outermost layer is allograft and/or autograft bone. In certain embodiments, the crosslink member may be constructed of a material comprising about 50% allograft and/or autograft bone and about 50% metal or metal alloy. In various embodiments, the metal or metal alloy may be titanium alloy, cobalt-chromium, niobium alloy, or tantalum alloy. Still referring to the crosslink member, the allograft and/or autograft bone may be cancellous or cortical bone. In another embodiment, the crosslink member is coated with an antibiotic solution. In another embodiment, the fenestration may be filled with stem cells. In various embodiments the fenestration may be filled with allograft and/or autograft bone. In another embodiment, the titanium or metal parts are replaced with carbon or graphite fiber reinforced parts in similar ratios as described above with the titanium embodiment.

Figure 6:
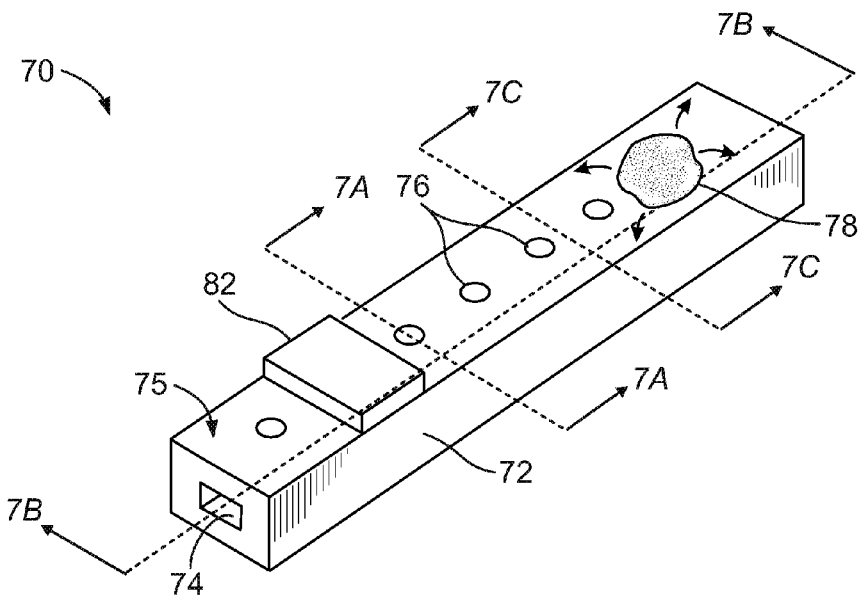
FIG. 6 shows an isometric view of a composite bar used with the invention.

FIG. 6 shows an isometric view of an example of a composite bar for use in an orthopedic surgical procedure, according to the present invention. Bar 70 comprises a load-bearing structural body 72, with a top side 75, a central cannulation 74 running along the long direction of the bar, a plurality of fenestrations 72 where each fenestration is a small hole that penetrates down from the top side 75, through structural layer 72, and into cannulation 74, where it stops there (it does not pass through to the bottom side in this example). FIG. 6 shows an outer layer of bone 82 in two different stages: (a) initial deposition of a bone growth mixture 78 on the top side 75; and (b) a final stage as a solid, full-thickness layer 82 of living bone tissue. Orthopedic bar 70 is constructed as a composite structure made of at least two different types of materials: (1) a rigid or semi-rigid load-bearing material (e.g., metal, ceramic, ceramic-metal composite, or a fiber-reinforced material, such as graphite fiber reinforced plastic, carbon-fiber composite, SiC-fiber reinforced SiC, etc.)), and (2) a more compliant (less rigid) material (e.g., polymer, allograft or autograft bone, which can be cancellous or cortical bone, graphite or carbon).

In some embodiments, orthopedic bar 70 can be made of a composite material comprising allograft and/or autograft bone and a metal or metal alloy. In some embodiments, the rigid or semi-rigid load-bearing material is a metal or metal alloy; and the more compliant (less rigid) material is allograft or autograft bone. In some embodiments, the metal or metal alloy is titanium alloy. In other embodiments, the rigid or semi-rigid load-bearing material comprises a fiber-reinforced material, with the fibers primarily aligned with the long direction of the composite bar 70.

Figure 7A:
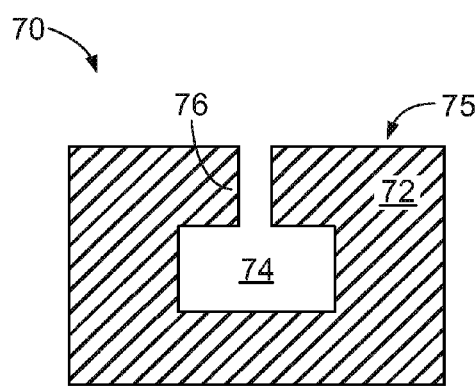
FIG. 7A is a cross-section view of the embodiment shown in FIG. 6 along Section 7A-7A.
Figure 7B:
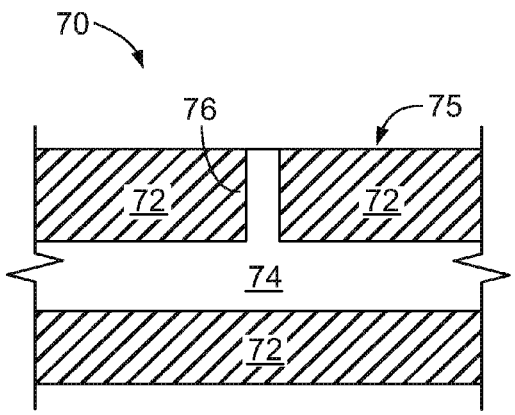
FIG. 7B is a cross-section view of the embodiment shown in FIG. 6 along Section 7B-7B.
Figure 7C:
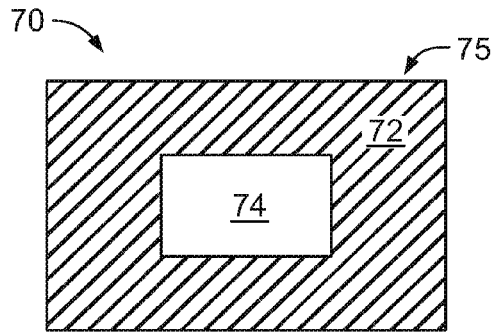
FIG. 7C is a cross-section view of the embodiment shown in FIG. 6 along Section 7C-7C.

Referring now to FIGS. 7A, 7B, and 7C, which show cross-section cuts through the bar at Section A-A, Section B-B, and Section B-B, respectively. The orthopedic bar 70 is constructed as a two-layer, skeleton-type, composite geometry, comprising: a central cannulation 74, which is initially empty, and which is surrounded by/defined by a structural, load-bearing body 72 made of a rigid or semi-rigid load-bearing material (as described above). FIG. 7B shows an example of a fenestration 76 that fluidically connects cannulation 74 to the upper surface 75 of body 72. In FIG. 7C, fenestration 76 does not show up.

Figure 8C:
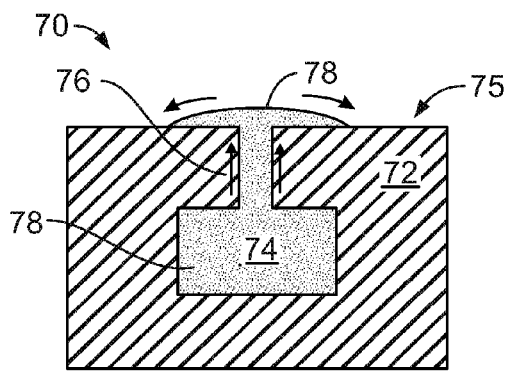
FIG. 8C is a cross-section view of the embodiment shown in FIG. 6 along Section 8C-8C after being filed with a bone growth mixture.
Figure 8C:
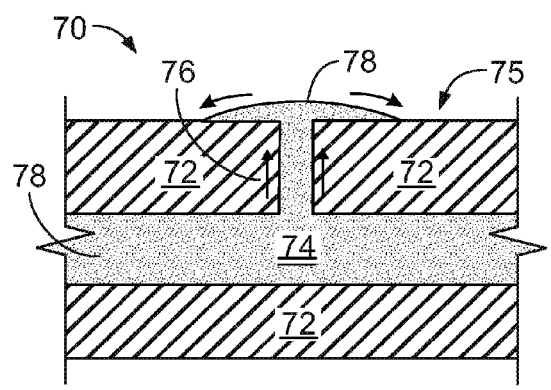
Figure 8C:
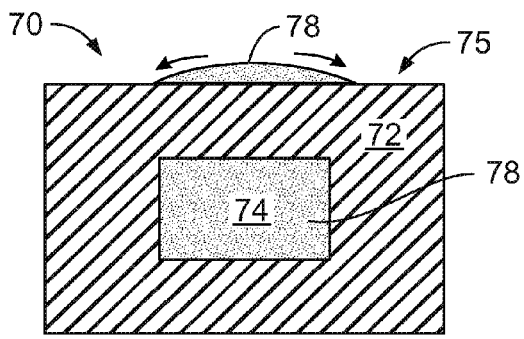

Next, in FIGS. 8A, 8B, and 8C, a bone growth mixture 78 (as described previously, comprising stem cells, particles of allograft or autograft bone, etc.) has been placed or injected into cannulation 74. The mixture 78 flows up through fenestration 76 (which can have a diameter small enough that capillary forces can drive the motion of fluid 78 from cannulation 74 onto upper surface 75. Once the mixture 78 has reached the upper surface 75, it can flow across the surface, as depicted in FIG. 8B.

Figure 9A:
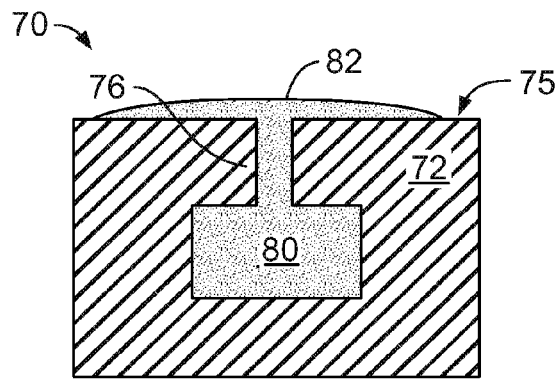
FIG. 9A is a cross-section view of the embodiment shown in FIG. 6 along Section 9A-9A after being filed with a bone growth mixture that has consolidated.
Figure 9B:
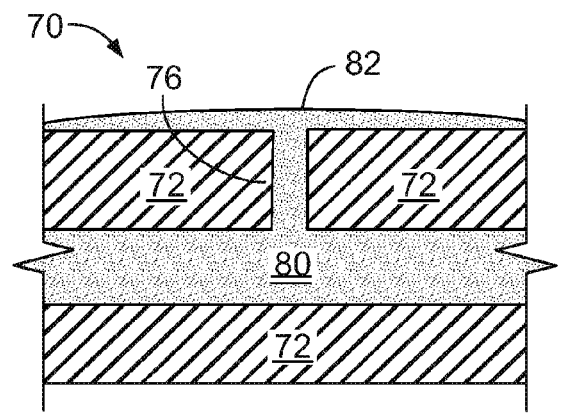
FIG. 9B is a cross-section view of the embodiment shown in FIG. 6 along Section 9B-9B after being filed with a bone growth mixture that has consolidated.
Figure 9C:
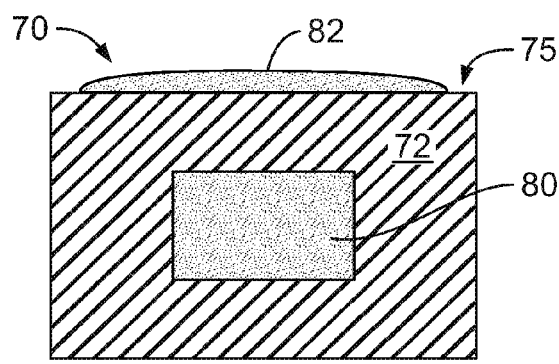
FIG. 9C is a cross-section view of the embodiment shown in FIG. 6 along Section 9C-9C after being filed with a bone growth mixture that has consolidated.

Finally, as shown in FIGS. 9A, 9B, and 9C, after a sufficient amount of time, bone growth mixture 78 has transformed into consolidated, living bone tissue 80, which has formed a uniform, outer layer 82 of living bone 80 covering the top side 75 of body 72, and connected to an inner layer 80 of living bone inside of cannulation 74 and fenestration 76.

In some of these embodiments of orthopedic bar 70, the composite configuration may comprise about 50% allograft and/or autograft bone, and about 50% metal or metal alloy. In other embodiments, each layer (core, middle, and outer) has approximately the same thickness as the other two layers (i.e., 33%, 33%, 33%). In other embodiments, the thickness of the different layers can be chosen to be any thickness that provides the necessary and/or optimum properties for a specific design. In other embodiments, the "metal or metal alloy" may comprise a titanium alloy, cobalt-chromium alloy, niobium alloy, tantalum alloy, or a stainless steel alloy. In another embodiment, the titanium or metal parts are replaced with carbon or graphite fiber reinforced parts in similar ratios as described above with the titanium embodiment. In some embodiments, an antibiotic coating can be applied to any of the surfaces of orthopedic bar 70.

Figure 10:
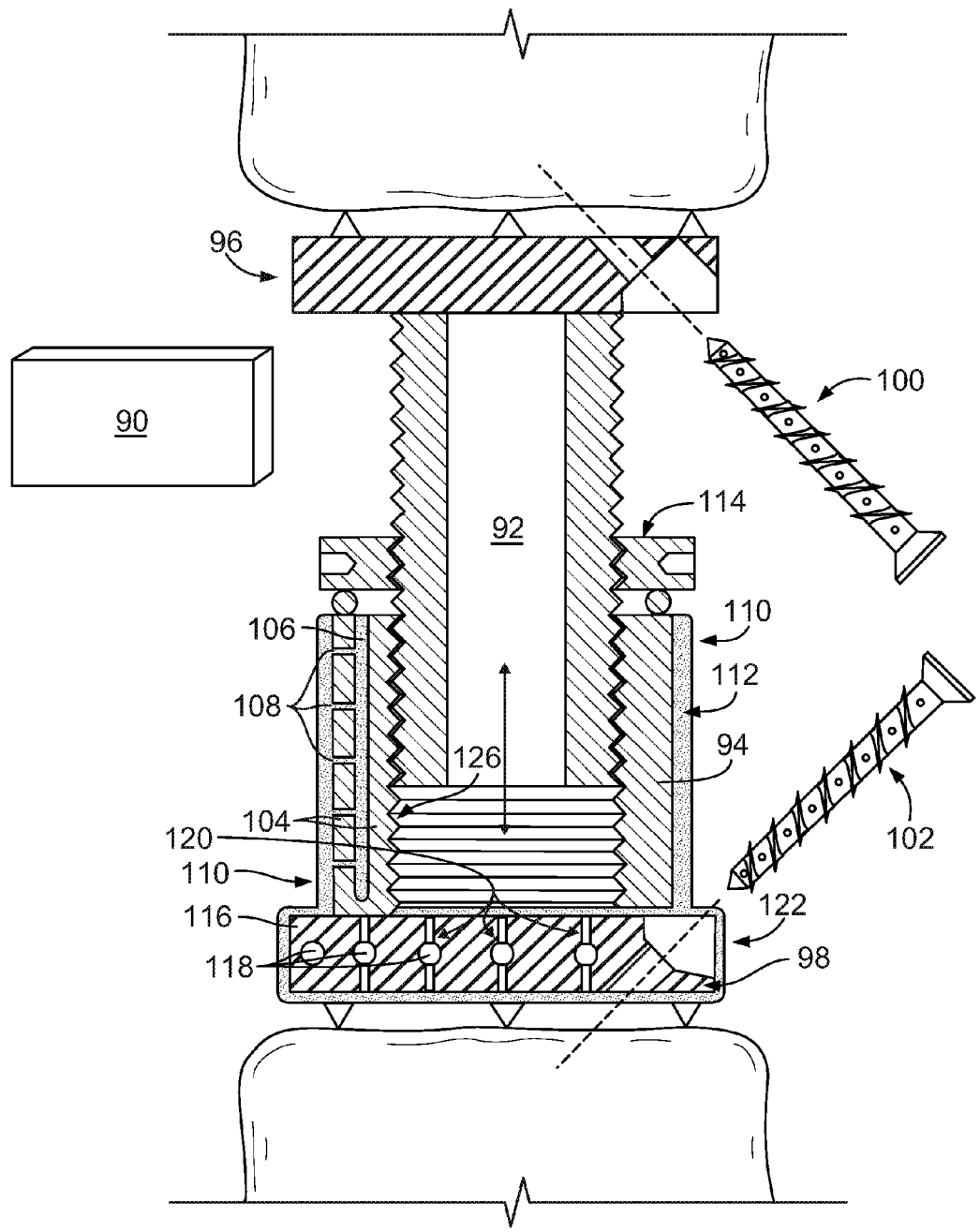
FIG. 10 is a cross-section view of a composite corpectomy cage.
Figure 11:
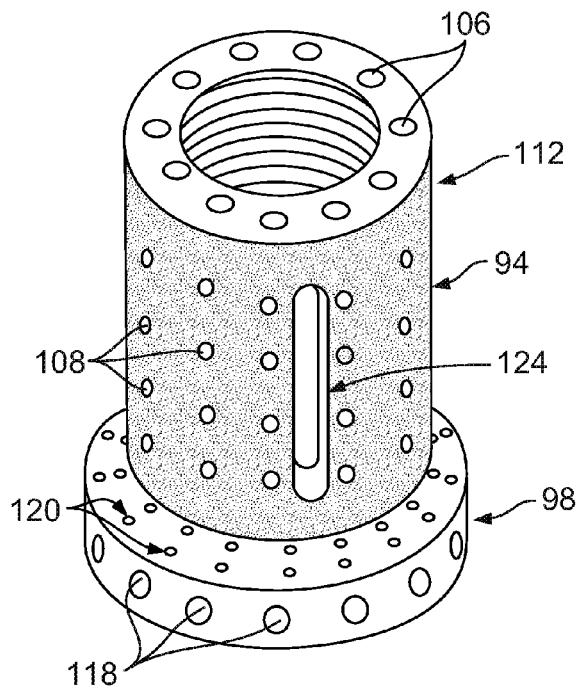
FIG. 11 shows an isometric view of an inferior support plate used with the invention.
Figure 12:
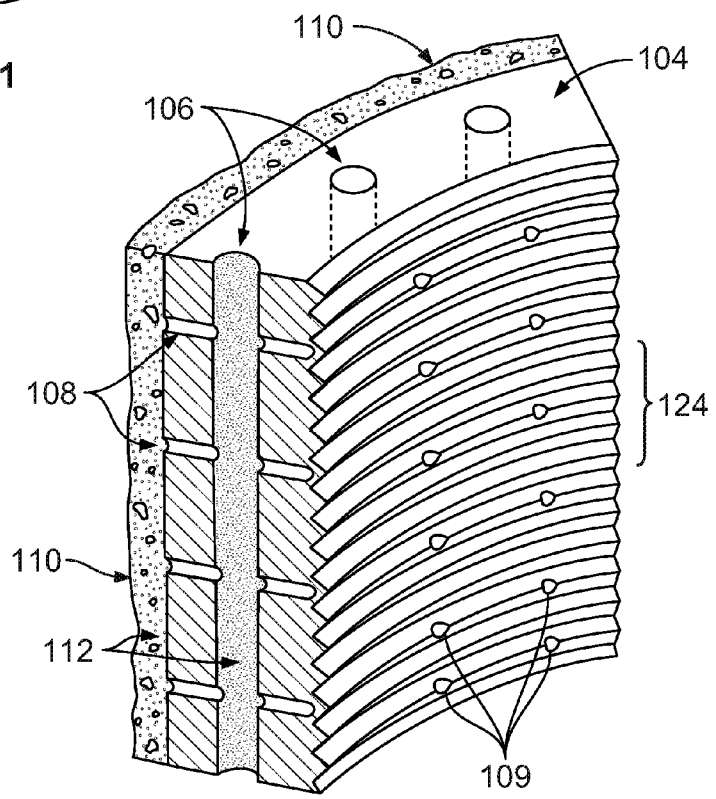
FIG. 12 shows an isometric, cutaway view of an outer corpectomy tube used with the invention.

FIGS. 10, 11 and 12 illustrate an example of a composite corpectomy cage, for use in a spinal implant procedure, where an entire vertebra is replaced with a structural body (i.e., corpectomy cage). The composite corpectomy cage 90 is similar to all of the previously described composite orthopedic devices.

FIG. 10 shows a cross-section view cut by a vertical plane passing through the device. This corpectomy cage 90 ("cage") comprises two, concentric cylinders, 92 and 94, that are engaged by helical threads. Rotation of an extension ring causes the inner cylinder 92 (extension tube) to move up or down relative to the outer cylinder 94. The top (superior) end of the inner cylinder is attached to the superior plate 96 (which can be a round disc). Likewise, the lower (inferior) end of the outer cylinder is attached to the inferior plate 98 (which can also be a round disc). A pair of composite bone screws, 100, 102, (according to the present invention) pass through the superior and inferior plates, 96 and 98, at roughly 45 degrees to the horizontal, respectively, and engage the vertebra bones above and below the cage, respectively. Each screw securely fastens it's respective plate to the solid bone of the end-plates of each adjoining vertebra. This geometry preserves the highly desirable "zero-profile" rule, where no part of the corpectomy cage protrudes anteriorly or posteriorly beyond its adjacent vertebra. Extension ring, 114, can be rotated to cause axial extension (or retraction) of the inner cylinder, relative to the outer cylinder.

Referring still to FIG. 10, the thick wall of the outer cylinder 94 contains the "triple layer" geometry of the present invention, which comprises a titanium alloy structural body 104 (cylinder) with a plurality of vertically-oriented cannulations 106 (channels) that are open at one or more ends; a plurality of radially-oriented fenestrations 108, and an outer layer of bone 110 (allograft and/or autograft bone), which can be about 1-2 mm thick. An antibiotic coating 112 can be disposed on any of the surfaces of the corpectomy cage 90.

The lower (inferior) support plate 98 also comprises the "triple layer" design of the present invention. The plate 98 comprises: a titanium alloy structural body 116 (disc), with a plurality of radial cannulations 118 that pass through the center of the disc; a plurality of vertically oriented fenestrations 120; and an outer layer of bone 122 (allograft and/or autograft bone), which can be about 1-2 mm thick. In a similar fashion (but not illustrated), the inner extension tube 92 and the superior support plate 96 can also be constructed of the "triple layer" geometry of the present invention.

In certain embodiments, the corpectomy cage 90 may be constructed of a material comprising about 50% allograft and/or autograft bone and about 50% metal or metal alloy. In various embodiments, the metal or metal alloy may be titanium alloy, cobalt-chromium, niobium alloy, or tantalum alloy. The allograft and/or autograft bone may be cancellous or cortical bone. In another embodiment, the corpectomy cage is coated with an antibiotic solution. In another embodiment, the fenestration may be filled with stem cells. In various embodiments the fenestration may be filled with allograft and/or autograft bone. In another embodiment, the titanium alloy structural parts are replaced with carbon or graphite fiber reinforced parts in similar ratios as described above with the titanium embodiment.

FIG. 11 shows an isometric view of the inferior support plate 98 (corpectomy base), attached to the outer corpectomy tube 94 (cylinder). In this view, the radial cannulations 118 and the vertical fenestrations 120 of the circular support base 98 can be seen. Also, in this view, the vertical cannulations 106 and the radial fenestrations 108 of the outer corpectomy tube 94 can be seen. The outer layer of bone is not shown, so that the underlying pattern of fenestration holes can be more easily visualized. An example of an optional vertical slot 124 is illustrated, which is cut through the wall of the outer tube (cylinder). This slot (which can comprise 2-8 slots, for example), allows for (1) a lighter-weight device, and (2) for direct fluid communication between the inside and outside volumes of the tube (e.g., to enhance bone graft growth and densification). Alternatively, optional large-diameter (e.g., 10 mm dia.) through-holes can be drilled in place of the optional vertical slots 124.

FIG. 12 shows an isometric, cutaway view of the outer corpectomy tube 94 (cylinder), showing the vertical cannulations 106 disposed inside of a titanium alloy structural body 104 (cylinder); a plurality of radial fenestrations 108, optionally passing completely through (109) the sidewall of the cylinder and into the internal threads 126; the outer layer of bone 110; and antibiotic coating(s) 112.

Other Methods

In various embodiments, the present invention provides a method of using a composite bone screw in a surgical procedure comprising; providing a composite bone screw as described above; and inserting said composite bone screw into a bone.

In various embodiments, the present invention provides a method of using a composite rod, bar, strip, or cross-link member in a surgical procedure comprising; providing a composite rod, bar, strip, or cross-link member as described above; and fastening the composite rod, bar, strip, or cross-link member to a bone.

In various embodiments, the present invention provides a method of using a composite plate in a surgical procedure comprising; providing a composite plate as described above; and fastening the composite plate to a bone.

In various embodiments, the present invention provides a method of using a composite spinal fusion interbody spacer in a surgical procedure comprising; providing a composite spinal fusion interbody spacer as described above; and fastening the composite spinal fusion interbody spacer to a bone, generally in the space in-between two adjacent vertebra when a disc has been removed.

OTHER EMBODIMENTS

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description, which do not depart from the spirit or scope of the present inventive discovery. Such modifications are also intended to fall within the scope of the appended claims.

All references cited in this specification are hereby incorporated by reference. The discussion of the references herein is intended merely to summarize the assertions made by their authors and no admission is made that any reference constitutes prior art relevant to patentability. Applicant reserves the right to challenge the accuracy and pertinence of the cited references.

Descriptive Trademarks

For purposes of establishing descriptive Trademarks, the Inventor herein has provided lists of desirable Trademarked orthopedic devices in Tables 1, 2, and 3 for use with the orthopedic devices and methods of the present invention, as follows:

TABLE 1

| Kaloostian ™ Trademarked Orthopedic Devices | | | |
|---|---|---|---|
| Orthopedic Device | Trademark-1 | Trademark-2 | Trademark-3 |
| Composite Bone Screw | Kaloostian ™ BoneScrew | K ™-BoneScrew | Kal ™-BoneScrew |

TABLE 1-continued

Kaloostian ™ Trademarked Orthopedic Devices

| Orthopedic Device | Trademark-1 | Trademark-2 | Trademark-3 |
|---|---|---|---|
| Polyaxial Composite Bone Screw | Kaloostian ™ PolyScrew | K ™-PolyScrew | Kal ™-PolyScrew |
| Composite Set Screw | Kaloostian ™ SetScrew | K ™-SetScrew | Kal ™-SetScrew |
| Composite Rod | Kaloostian ™ Rod | K ™-Rod | Kal ™-Rod |
| Composite Plate | Kaloostian ™ Plate | K ™-Plate | Kal ™-Plate |
| Composite Bar | Kaloostian ™ Bar | K ™-Bar | Kal ™-Bar |
| Composite Crosslink | Kaloostian ™ Crosslink | K ™-Crosslink | Kal ™-Crosslink |
| Composite Tube | Kaloostian ™ Tube | K ™-Tube | Kal ™-Tube |
| Composite Disc | Kaloostian ™ Disc | K ™-Disc | Kal ™-Disc |
| Composite Interbody | Kaloostian ™ Interbody | K ™-Interbody | Kal ™-Interbody |
| Composite Corpectomy Cage | Kaloostian ™ Corpectomy Cage | K ™-Corpectomy Cage | Kal ™-Corpectomy Cage |

TABLE 2

Kaloostian ™ Trademarked Carbon Fiber Technology Orthopedic Devices

| Carbon Fiber Technology Orthopedic Device | Trademark-1 | Trademark-2 | Trademark-3 |
|---|---|---|---|
| Composite Bone Screw | Kaloostian ™ Carbon Fiber Screw | K ™-CF BoneScrew | Kal ™-CF BoneScrew |
| Polyaxial Composite Bone Screw | Kaloostian ™ Carbon Fiber PolyScrew | K ™-CF PolyScrew | Kal ™-CF PolyScrew |
| Composite Set Screw | Kaloostian ™ Carbon Fiber SetScrew | K ™-CF SetScrew | Kal ™-CF SetScrew |
| Composite Rod | Kaloostian ™ Carbon Fiber Rod | K ™-CF Rod | Kal ™-CF Rod |
| Composite Plate | Kaloostian ™ Carbon Fiber Plate | K ™-CF Plate | Kal ™-CF Plate |
| Composite Bar | Kaloostian ™ Carbon Fiber Bar | K ™-CF Bar | Kal ™-CF Bar |
| Composite Crosslink | Kaloostian ™ Carbon Fiber Crosslink | K ™-CF Crosslink | Kal ™-CF Crosslink |
| Composite Tube | Kaloostian ™ Carbon Fiber Tube | K ™-CF Tube | Kal ™-CF Tube |
| Composite Disc | Kaloostian ™ Carbon Fiber Disc | K ™-CF Disc | Kal ™-CF Disc |
| Composite Interbody | Kaloostian ™ Carbon Fiber Interbody | K ™-CF Interbody | Kal ™-CF Interbody |
| Composite Corpectomy Cage | Kaloostian ™ Carbon Fiber Corpectomy Cage | K ™-CF Corpectomy Cage | Kal ™-CF Corpectomy Cage |

TABLE 3

Kaloostian ™ Trademarked Pulsed Radiofrequency Stimulation (RFS) Technology Orthopedic Devices

| Pulsed Radiofrequency Stimulation (RFS) Technology Orthopedic Device | Trademark-1 | Trademark-2 | Trademark-3 |
|---|---|---|---|
| Composite Bone Screw | Kaloostian ™ Radiofrequency Stimulation Screw | K ™-RFS BoneScrew | Kal ™-RFS BoneScrew |
| Polyaxial Composite Bone Screw | Kaloostian ™ Radiofrequency Stimulation PolyScrew | K ™-RFS PolyScrew | Kal ™-RFS PolyScrew |
| Composite Set Screw | Kaloostian ™ Radiofrequency Stimulation SetScrew | K ™-RFS SetScrew | Kal ™-RFS SetScrew |
| Composite Rod | Kaloostian ™ Radiofrequency Stimulation Rod | K ™-RFS Rod | Kal ™-RFS Rod |
| Composite Plate | Kaloostian ™ Radiofrequency Stimulation Plate | K ™-RFS Plate | Kal ™-RFS Plate |
| Composite Bar | Kaloostian ™ Radiofrequency Stimulation Bar | K ™-RFS Bar | Kal ™-RFS Bar |
| Composite Crosslink | Kaloostian ™ Radiofrequency Stimulation Crosslink | K ™-RFS Crosslink | Kal ™-RFS Crosslink |
| Composite Tube | Kaloostian ™ Radiofrequency Stimulation Tube | K ™-RFS Tube | Kal ™-RFS Tube |
| Composite Disc | Kaloostian ™ Radiofrequency Stimulation Disc | K ™-RFS Disc | Kal ™-RFS Disc |
| Composite Interbody | Kaloostian ™ Radiofrequency Stimulation Interbody | K ™-RFS Interbody | Kal ™-RFS Interbody |
| Composite Corpectomy Cage | Kaloostian ™ Radiofrequency Stimulation Corpectomy Cage | K ™-RFS Corpectomy Cage | Kal ™-RFS Corpectomy Cage |

What is claimed is:

1. A composite orthopedic bone screw for use in a surgical procedure comprising:
   a. a polyaxial drive head; and
   b. a body comprising:
      i. a distal tip; and
      ii. an outwardly cylindrical threaded shaft extending from the drive head to the tip,
   wherein the shaft defines a cannulation extending from the drive head along at least a portion of the length of the shaft;

wherein the cannulated portion of the shaft contains at least one fenestration connected to the cannulation; and wherein the bone screw is constructed of a material comprising allograft and/or autograft bone and a metal or metal alloy.

2. The bone screw according to claim 1, wherein the bone screw is constructed of a material comprising a core and two layers; wherein the core is allograft and/or autograft bone, the middle layer is a metal or metal alloy, and the outermost layer is allograft and/or autograft bone.

3. The bone screw according to claim 1, wherein the bone screw is constructed of a material comprising about 50% allograft and/or autograft bone and about 50% metal or metal alloy.

4. The bone screw according to claim 1, wherein the metal or metal alloy is selected from the group consisting of a titanium alloy, cobalt-chromium, niobium alloy, and tantalum alloy.

5. The bone screw according to claim 1, wherein the bone screw has a torque shear strength of at least 0.10-0.20 newton-meters.

6. The bone screw according to claim 1, wherein the bone screw has a pullout force of 500-700 Newtons.

7. The bone screw according to claim 1, wherein the threaded shaft tapers outwardly adjacent to the drive head to form a tapered undercut for the drive head.

8. The bone screw according to claim 1, wherein:

the cannulated portion of the shaft contains a plurality of fenestrations, and the fenestrations are spaced so as to occur every two full rotations of the threaded shaft.

9. The bone screw according to claim 1, wherein the allograft and/or autograft bone is cancellous or cortical bone.

10. The bone screw according to claim 1, wherein the bone screw is coated with an antibiotic solution.

11. The bone screw according to claim 1, wherein the cannulated portion of the shaft is filled with a mixture of stem cells and allograft and/or autograft bone.

* * * * *